(12) United States Patent
Høgset et al.

(10) Patent No.: US 11,648,287 B2
(45) Date of Patent: May 16, 2023

(54) COMPOSITION FOR THE TREATMENT OF INTRACELLULAR BACTERIAL INFECTION

(71) Applicants: PCI Biotech AS, Oslo (NO); Academisch Medisch Centrum, Amsterdam (NL)

(72) Inventors: Anders Høgset, Oslo (NO); Sebastian A. J. Zaat, Amsterdam (NL); Xiaolin Zhang, Amsterdam (NL)

(73) Assignees: ACADEMISCH MEDISCH CENTRUM, Amsterdam (NL); PCI BIOTECH AS, Oslo (NO)

( * ) Notice: Subject to any disclaimer, the term of this patent is extended or adjusted under 35 U.S.C. 154(b) by 0 days.

(21) Appl. No.: 16/762,339

(22) PCT Filed: Nov. 9, 2018

(86) PCT No.: PCT/EP2018/080832
§ 371 (c)(1),
(2) Date: May 7, 2020

(87) PCT Pub. No.: WO2019/092215
PCT Pub. Date: May 16, 2019

(65) Prior Publication Data
US 2020/0268834 A1    Aug. 27, 2020

(30) Foreign Application Priority Data
Nov. 10, 2017  (GB) .................................... 1718631

(51) Int. Cl.
| A61K 38/14 | (2006.01) |
|---|---|
| A61K 45/06 | (2006.01) |
| A61K 41/00 | (2020.01) |
| A61P 31/04 | (2006.01) |
| A61K 31/7036 | (2006.01) |

(52) U.S. Cl.
CPC .......... *A61K 38/14* (2013.01); *A61K 31/7036* (2013.01); *A61K 41/0071* (2013.01); *A61P 31/04* (2018.01); *A61K 45/06* (2013.01)

(58) Field of Classification Search
CPC ............ A61K 2300/00; A61K 31/7036; A61K 38/14; A61K 41/0071; A61K 45/06; A61K 41/00; A61P 31/04
See application file for complete search history.

(56) References Cited

U.S. PATENT DOCUMENTS

| 5,941,701 A * | 8/1999 | Moran ..................... A61D 5/00 |
|---|---|---|
| | | 433/1 |
| 6,610,298 B2 * | 8/2003 | Hasan ................. A61K 41/0071 |
| | | 424/178.1 |
| 2002/0183808 A1 | 12/2002 | Biel |
| 2009/0233887 A1 * | 9/2009 | Shalaby ................. C08G 18/12 |
| | | 514/154 |
| 2009/0304803 A1 | 12/2009 | Hasan |
| 2010/0121255 A1 * | 5/2010 | Rimington .............. A61P 17/12 |
| | | 604/20 |

FOREIGN PATENT DOCUMENTS

| JP | 2008-505633 | 2/2008 |
|---|---|---|
| WO | 96/07432 | 3/1996 |
| WO | 99/30686 | 6/1999 |
| WO | 00/23117 | 4/2000 |
| WO | 00/54802 | 9/2000 |
| WO | 02/44396 | 6/2002 |
| WO | 03/020309 | 3/2003 |
| WO | 2005/034855 | 4/2005 |
| WO | 2006/003463 | 1/2006 |
| WO | 2010/014676 | 2/2010 |
| WO | 2011/018635 | 2/2011 |
| WO | 2011/018636 | 2/2011 |
| WO | 2015/028574 | 3/2015 |

OTHER PUBLICATIONS

Q Fever from Merck Manual, pp. 1-3. Accessed Nov. 23, 2021. (Year: 2021).*
Ulcerative Colitis from Merck Manual, pp. 1-7. Accessed Nov. 23, 2021. (Year: 2021).*
Periodontitis from Merck Manual, pp. 1-4. Accessed Nov. 23, 2021. (Year: 2021).*
Bacterial Infections from Merck Manual, pp. 1-3. Accessed Nov. 23, 2021. (Year: 2021).*
Intracellular Bacterial Infection from Merck Manual, pp. 1-3. Accessed Nov. 23, 2021. (Year: 2021).*
Roy et al., "Aerosolized Gentamicin Reduces the Burden of Tuberculosis in a Murine Model," Antimicrobial Agents and Chemotherapy, Nov. 23, 2011, 883-886. (Year: 2011).*
International Search Report and Written Opinion of the International Searching Authority, dated Feb. 15, 2019 in corresponding International Patent Application No. PCT/EP2018/080832.
Zhang et al., "Photochemical internalization enhances cytosolic release of antibiotic and increases its efficacy against staphylococcal infection", Journal of Controlled Release, 283: 214-222 (2018).
Dastgheyb, Sana S. et al., "Photo-activated porphyrin in combination with antibiotics: Therapies against *Staphylococci*", Journal of Photochemistry and Photobiology, Biology, 2013, vol. 129, pp. 27-35.

(Continued)

*Primary Examiner* — Julie Ha
(74) *Attorney, Agent, or Firm* — Wenderoth, Lind & Ponack, L.L.P.

(57) ABSTRACT

A method of treating or preventing an intracellular bacterial infection, comprising contacting the cell(s) which are infected with an antibacterial agent and a photosensitizing agent and irradiating the cell(s) with light of a wavelength effective to activate the photosensitizing agent, wherein the antibacterial agent is released into the cytosol of the cell(s) and kills, damages or prevents the replication of bacteria in said cell(s) is described. Related uses, and compositions, products and kits for the same are further described.

23 Claims, 7 Drawing Sheets

(56) References Cited

OTHER PUBLICATIONS

Figure 1:
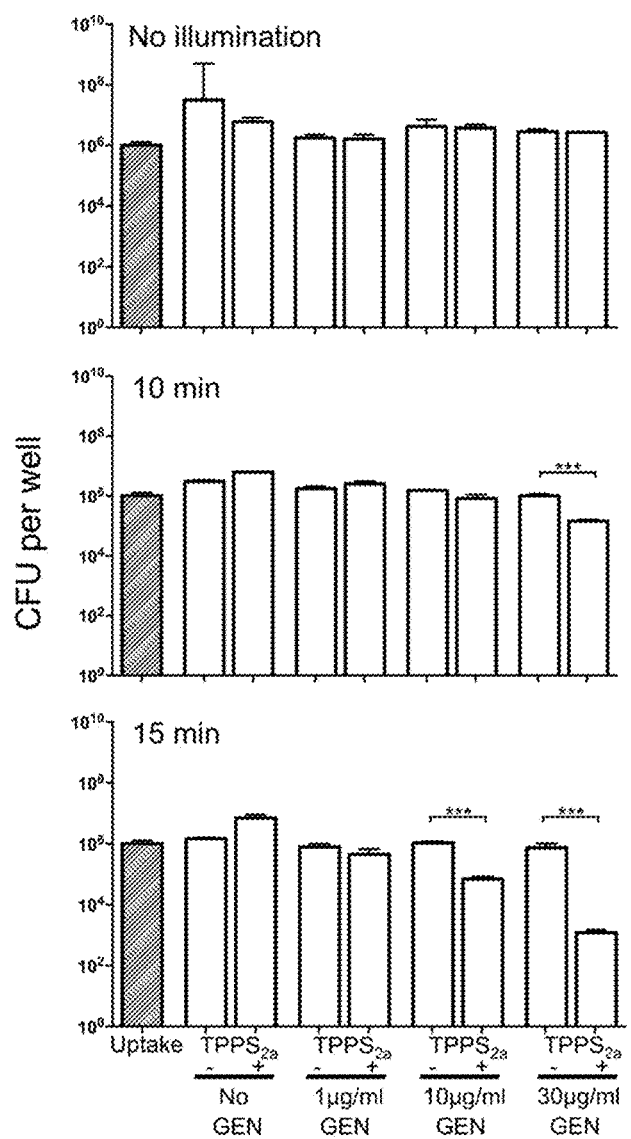

Cassidy, Corona M. et al., "Photodynamic Antimicrobial Chemotherapy (PACT) in combination with antibiotics for treatment of *Burkholderia cepacia* complex infection", Journal of Photochemistry and Photobiology B: Biology, 2012, vol. 106, pp. 95-100.
Barra, Federica et al., "Photodynamic and Antibiotic Therapy in Combination to Fight Biofilms and Resistant Surface Bacterial Infections", International Journal of Molecular Sciences, 2015, vol. 16, pp. 20417-20430.
Di Poto, Antonella et al., "The effect of photodynamic treatment combined with antibiotic action or host defence mechanisms on *Staphylococcus aureus* biofilms", Biomaterials, 2009, vol. 30, pp. 3158-3166.
Collins, Tracy L. et al., "The Effect of a Cationic Porphyrin on *Pseudomonas aeruginosa* Biofilms", Current Microbiology, 2010, vol. 61, pp. 411-416.
Høgset, Andres et al., "Photochemical internalisation in drug and gene delivery", Advanced Drug Delivery Review, 2004, vol. 56, pp. 95-115.
Abed, Nadia et al., "Nanocarriers for antibiotics: A promising solution to treat intracellular bacterial infections", International Journal of Antimicrobial Agents, 2014, vol. 43, No. 6, pp. 485-496.
Xiong, Meng-Hua et al., "Delivery of antibiotics with polymeric particles", Advanced Drug Delivery Reviews, 2014, vol. 78, pp. 63-76.
Briones, Elsa et al., "Delivery systems to increase the selectivity of antibiotics in phagocytic cells", Journal of Controlled Release, 2008, vol. 125, No. 3, pp. 210-227.
Tulkens, P.M., "Intracellular distribution and Activity of Antibiotics", European Journal of Clinical Microbiology and Infectious Diseases, Feb. 1991, vol. 10, No. 2, pp. 100-106.
Carryn, Stéphane et al., "Intracellular pharmacodynamics of antibiotics", Infectious Disease Clinics of North America, 2003, vol. 17, No. 3, pp. 615-634.
Seral, Cristina et al., "Influence of P-glycoprotein and MRP efflux pump inhibitors on the intracellular activity of azithromycin and ciprofloxacin in macrophages infected by *Listeria monocytogenes* or *Staphylococcus aureus*", Journal of Antimicrobial Chemotherapy, 2003, vol. 51, No. 5, pp. 1167-1173.
Carryn, Stéphane et al., "Comparative Intracellular (THP-1 Macrophage) and Extracellular Activities of β-Lactams, Azithromycin, Gentamicin, and Fluoroquinolones against *Listeria monocytogenes* at Clinically Relevant Concentrations", Antimicrobial Agents and Chemotherapy, Jul. 2002, vol. 46, No. 7, pp. 2095-2103.
Seral, Cristina et al., "Influence of P-glycoprotein inhibitors on accumulation of macrolides in J774 murine macrophages", Antimicrobial Agents and Chemotherapy, Mar. 2003, vol. 47, No. 3, pp. 1047-1051.
Forrest, Graeme N. et al., Rifampin Combination Therapy for Nonmycobacterial Infections, Clinical Microbiology Reviews, 2010, vol. 23, No. 1, pp. 14-34.
Lehar, Sophie M. et al., "Novel antibody-antibiotic conjugate eliminates intracellular *S. aureus*", Nature, 2015, vol. 527, No. 7578, pp. 323-328.
Randhawa, Harmandeep Kaur et al., "Cell-penetrating peptide and antibiotic combination therapy: a potential alternative to combat drug resistance in methicillin-resistant *Staphylococcus aureus*", Appl. Microbiol. Biotechnol., 2016, vol. 100, No. 9, pp. 4073-4083.
Brezden, Anna et al., "Dual Targeting of Intracellular Pathogenic Bacteria with a Cleavable Conjugate of Kanamycin and an Antibacterial, Cell Penetrating Peptide", J. Am. Chem. Soc., 2016, vol. 138, No. 34, pp. 10945-10949.
Maisch, Tim et al., "Antibacterial photodynamic therapy in dermatology", Photochem. Photobiol. Sci., 2004, vol. 3, No. 10, pp. 907-917.
Liu, Yao et al., "Antibacterial photodynamic therapy: overview of a promising approach to fight antibiotic-resistant bacterial infections", Journal of Clinical and Translational Research, 2015, vol. 1, No. 3, pp. 140-167.
Selbo, Pål Kristian et al., "Strongly amphiphilic photosensitizers are not substrates of the cancer stem cell marker ABCG2 and provides specific and efficient light-triggered drug delivery of an EGFR-targeted cytotoxic drug", Journal of Controlled Release, 2012, vol. 159, pp. 197-203.
Barcia-Macay, Maritza et al., Pharmacodynamic Evaluation of the Intracellular Activities of Antibiotics against *Staphylococcus aureus* in a Model of THP-1 Macrophages, Antimicrobial Agents and Chemotherapy, 2006, vol. 50, No. 3, pp. 841-851.
Bernardo, John et al., "Initial Cytoplasmic and Phagosomal Consequences of Human Neutrophil Exposure to *Staphylococcus epidermidis*", Cytometry Part A, 2010, vol. 77A, No. 3, pp. 243-252.
"Medications and other Agents that Increase Sensitivity to Light", Wisconsin Department of Health Services, 2015, pp. 1-45.
Mathews, Marlon S. et al., "Photochemical internalization of bleomycin for glioma treatment", Journal of Biomedical Optics, 2012, vol. 17, No. 5, pp. 1-9.
Czyż, Daniel M. et al., "Host-Directed Antimicrobial Drugs with Broad-Spectrum Efficacy against Intracellular Bacterial Pathogens", MBIO, Jul./Aug. 2014, vol. 5, No. 4, pp. 1-14.
Gajdács, Márió et al., "The Role of Drug Repurposing in the Development of Novel Antimicrobial Drugs: Non-Antibiotic Pharmacological Agents as Quorum Sensing-Inhibitors", Antibiotics, 2019, vol. 8, No. 270, pp. 1-18.
Norum, Ole-Jacob et al., "Photochemical Internalization of Bleomycin is Superior to Photodynamic Therapy Due to the Therapeutic Effect in the Tumor Periphery", Photochemistry and Photobiology, 2009, vol. 85, No. 3, pp. 740-749.

\* cited by examiner

A

B

Vancomycin, BODIPY® FL without PCI

Vancomycin, BODIPY® FL with PCI (120 s illumination)

COMPOSITION FOR THE TREATMENT OF INTRACELLULAR BACTERIAL INFECTION

The present invention relates to a method of treating intracellular bacterial infections using a photochemical internalization method to introduce an antibacterial agent to kill the bacteria. The methods have particular utility in treating hard to treat infections such as those which occur in biomaterial-associated infections.

Intracellular survival of bacterial pathogens (e.g. *Mycobacterium tuberculosis, Pseudomonas aeruginosa, Escherichia coli,* and *Staphylococcus aureus*) is a notorious cause of many infectious diseases (Abed & Couvreur, 2014, *Int. J. Antimicrob. Ag.,* 43(6), p485-496; Xiong et al., 2014, *Adv. Drug Deliver. Rev.,* 7, p63-76; Briones et al., 2008, *J. Control Release,* 125(3), p210-227). For instance, *S. aureus* may cause a wide variety of skin or tissue infections as well as life-threatening invasive diseases such as bacteremia, biomaterial-associated infection, diabetic foot infection, endocarditis and osteomyelitis (Lew & Waldvogel, 2004, *Lancet,* 364(9431), p369-379; Busscher et al., 2012, *Sci. Transl. Med.,* 4(153); von Eiff et al., 2002, *Lancet Infect. Dis.,* 2(11), p677-685; Lipsky et al., 2004, *Clin. Infect. Dis.,* 39(7), p885-910; Saginur & Suh, 2008, *Int. J. Antimicrob. Agents.,* 32 Suppl 1, S21-25; Dhawan et al., 1998, *Infect. Immun.,* 66(7), p3476-3479).

Several in vitro, in vivo and clinical studies have provided evidence that macrophages and neutrophils may become niches for *S. aureus* to survive and evade host immune defence (Prajsnar et al., 2008, *Cell Microbiol.,* 10(11), p2312-2325; Tan et al., 2013, *Int. Forum Allergy Rh.,* 3(4), p261-266; Surewaard et al., 2016, *J. Exp. Med.,* 213(7), p1141-1151; and Seral et al., 2003, *Antimicrobial agents and chemotherapy,* 47(7), p2283-2292). Moreover, under some conditions, such as after implantation of medical devices, even the commensal *Staphylococcus epidermidis,* which usually has low pathogenicity, can persist intracellularly in macrophages and colonize healthy cells and uninfected tissue (Riool et al., 2014, *Acta Biomater.,* 10(12), p5202-5212; Broekhuizen et al., 2008, *Crit. Care Med.,* 36(8), p2395-2402; Broekhuizen et al., 2010, *Infect. Immun.,* 78(3), p954-962; and Zaat et al., 2010, *Future Microbiol.,* 5(8), p1149-1151). Consequently, these intracellular reservoirs of *S. aureus* and *S. epidermidis* or other bacterial species may cause the occurrence or recurrence of intracellular infection-associated diseases.

It is furthermore known that some bacteria remain in phagosomes and prevent fusion of these phagosomes with lysosomes. Examples of bacteria which adopt this strategy include *Mycobacterium tuberculosis* (the cause of the devastating and widespread disease of tuberculosis) and *Coxiella burnetti* (the cause of Q-fever).

Intracellular infection is usually very difficult to treat, since the majority of existing antibiotics has limited intracellular activity (Abed & Couvreur, 2014 supra; Xiong et al., 2014, supra; Briones et al., 2008, supra; Tulkens, 1991, *Eur. J. Clin. Microbiol.,* 10(2), p100-106 and Carryn et al., 2003, *Infect. Dis. Clin. N. Am.,* 17(3), p615-634). Beta-lactam antibiotics and aminoglycosides have low penetration into eukaryotic cells (Abed & Couvreur, 2014, supra; Tulkens, 1991, supra; Carryn et al., 2003, supra; Seral et al., 2003, *J. Antimicrob. Chemoth.,* 51(5), p1167-1173; and Carryn et al., 2002, *Antimicrob. Agents Ch.,* 46(7), p2095-2103), and although fluoroquinolones and macrolides can pass the eukaryotic cell membrane, they show low intracellular retention (Seral et al., 2003, supra; and Seral et al., 2003, *Antimicrob. Agents Ch.,* 47(3), p1047-1051). Rifampicin has good intracellular penetrating capacity, but is subject to very high frequencies of resistance development when used as single antibiotic. Therefore combination therapy of rifampicin with other antibiotics is mandatory (Forrest & Tamura, 2010, *Clin. Microbiol. Rev.,* 23(1), p14-34). However, even such combination therapy may fail to eliminate intracellular infection (Burns, 2006, *Scand. J. Infect. Dis.,* 38(2), p133-136). Intracellular pathogens may also develop resistance to certain antibiotics, since the low intracellular concentrations provide a selective condition for bacterial cells with reduced susceptibility (Baharoglu et al., 2013, *Plos Genet.,* 9(4), e1003421).

Several delivery systems based on liposomes, polymer micro-/nanoparticles and biological vehicles for different antibiotics with poor intracellular activity have been developed (Abed & Couvreur, 2014, supra; Xiong et al., 2014, supra; Lehar et ab., 2015, *Nature,* 527(7578), p323-328; Randhawa et al., 2016, *Appl. Microbiol. Biotechnol.,* 100(9), p4073-4083; and Brezden et al., 2016, *J. Am. Chem. Soc.,* 138(34), p10945-10949). However, the development of such systems and antibiotic conjugates is very complex.

As a potential strategy against multi-resistant bacteria, antibacterial photodynamic therapy (PDT) has been used in topical infections such as infected skin wounds (Maisch et al., 2004, *Photoch. Photobio. Sci.,* 3(10), p907-917; and Liu et al., 2015, *J. Clin. Transl. Research,* 1(3), p140-167).

PDT therapy is based on the employment of photosensitive agents (photosensitizers, PS) in combination with light. PS can accumulate in the cytoplasmic membrane of bacteria and actively kill them by the induced reactive oxygen reaction upon illumination of the site of treatment. However, only bacteria in the direct vicinity of the photosensitizer are killed.

Thus, novel antibiotics and/or new techniques for killing intracellular bacteria are urgently required.

The present invention provides a new method for killing intracellular bacteria which involves the use of photochemical internalization (PCI) and an antibacterial agent. PCI was developed to allow internalization of molecules, e.g. for treatment of several types of tumours (Selbo et al., 2010, *J. Control. Release,* 148(1), p2-12; and Høgset A, et al., 2004, *Adv. Drug Deliver. Rev.,* 56(1), p95-115). In PCI, photosensitizers specifically localize in membranes of endocytic vesicles and disrupt these membranes (partially) upon illumination, causing cytosolic release of molecules.

Surprisingly it has now been found that PCI of antibacterial agents provides a simple mechanism for killing intracellular bacteria.

PCI methods provide a mechanism for introducing molecules into the cytosol of a cell in a manner which does not result in widespread cell destruction or cell death if the methodology is suitably adjusted to avoid excessive toxic species production, e.g. by lowering illumination times or photosensitizer dose. The basic method of photochemical internalisation (PCI), is described in WO 96/07432 and WO 00/54802, which are incorporated herein by reference. In such methods, the molecule to be internalised (which in the present invention would be the antibacterial agent), and a photosensitizing agent are brought into contact with a cell. The photosensitizing agent and the molecule to be internalised are taken up into a cellular membrane-contained subcompartment within the cell, i.e. they are endocytosed into an intracellular vesicle (e.g. a lysosome or endosome). On exposure of the cell to light of the appropriate wavelength, the photosensitizing agent is activated which directly or indirectly generates reactive oxygen species which disrupt the intracellular vesicle's membranes. This allows the internalized molecule to be released into the cytosol. It was found that in such a method the functionality or the viability of the majority of the cells was not deleteriously affected.

This method of the invention is particularly advantageous because it is not a complex method and may be used with a variety of antibacterial agents and different target bacteria. It also allows the use of lower concentrations of the antibacterial agent than is required for conventional methods, whilst achieving effective antibiotic effects. This prevents resistance development. Furthermore, the timing and location of irradiation to release the molecules may be controlled such that it is released only at the time and location that is desired to achieve the required effects. As such, exposure of cells to the various components is minimised, and undesirable side effects are minimised. This is in contrast to the standard techniques for antibacterial treatment, where it is not possible to control the timing and location of the release of the various components and high concentrations of the various components and/or their carriers are needed.

Infectious diseases associated with intracellular survival of bacterial pathogens can occur or relapse at different sites of the human body (e.g. skin, deep tissues, urinary tract and lung). In addition to professional phagocytes, non-professional phagocytic cells such as epithelial cells, endothelial cells, osteoblasts and fibroblasts also can be niches of intracellular bacteria. The PCI method of the invention may be achieved at a specific location by applying light at the site of infection or at the location of the cells in which intracellular bacteria reside. In this way, the method may be used for treatment of (sub)cutaneous skin or mucosal infections/damages such as chronic wounds, ulcers, abscesses and diabetic foot infection as well as oral and nasal infections such as chronic rhinosinusitis and periodontitis, where the site of infection is relatively accessible for light. Infection in internal organs (e.g. lungs) or in deep tissue areas may be treated using light administered by fiber optic devices, for example.

As described in the Examples herein, the antimicrobial efficacy of antibacterial agents against intracellular *Staphylococci* with and without the use of PCI was evaluated in vitro in mouse macrophages and in vivo using a zebrafish embryo model, a whole animal system suitable for studying *Staphylococcal* infection (Prajsnar et al., 2008, supra; Veneman et al., 2013, *BMC Genomics*, 14, p255; and Prajsnar et al., 2012, *Cell Microbiol.*, 14(10), p1600-1619). To the best of our knowledge, this is the first teaching of the use of PCI in an entirely new application field, i.e. for antibiotic treatment of (intracellular) infection.

Whilst not wishing to be bound by theory, the likely mechanism of photochemical internalization (PCI) of antibacterial agents to combat intracellular bacteria relies, in the first step, on cellular uptake of antibacterial agents and photosensitizers (PS) and optionally bacteria. The PS localizes in vesicle membranes during the formation of endosomes/phagosomes containing the antibacterial agent. The antibacterial agents are released by activation of the PS (by disrupting the membranes of endosomes/phagosomes upon illumination) into the cytosol where they may come into contact with bacteria (present by co-internalization or pre-existing in the cells). The PS are also dissociated from the membrane and may be re-located to other endosomes/phagosomes that may contain antibacterial agents and/or bacteria during the illumination period thereby causing release of the bacteria/antibacterial agents in those endosomes/phagosomes into the cytosol. It is also possible that during PCI the vesicles ruptured by the light-activation of photosensitizer might intracellularly fuse with intact other vesicles to cause the intact ones also to become leaky/ruptured, even without additional illumination. Contact of the antibacterial agents with bacteria within the cytosol allows intracellular antibacterial action of the antibacterial agents.

Thus, in a first aspect, the present invention provides a method of treating or preventing an intracellular bacterial infection, comprising contacting the cell(s) which are infected with an antibacterial agent and a photosensitizing agent and irradiating the cell(s) with light of a wavelength effective to activate the photosensitizing agent, wherein the antibacterial agent is released into the cytosol of the cell(s) and kills, damages or prevents the replication of bacteria in said cell(s).

This method may be performed in vitro, but is preferably performed in vivo and said cell(s) is in a subject.

Preferably the method (or uses described herein) prevent the development of bacterial resistance. They may be used against antibacterial or antibiotic resistant bacteria.

In such methods the photosensitizing agent and the antibacterial agent, are each taken up into an intracellular vesicle; and when the cell is irradiated the membrane of the intracellular vesicle is disrupted releasing the molecules into the cytosol of the cell.

The different components may be taken up into the same or a different intracellular vesicle relative to each other. It has been found that active species produced by photosensitizers may extend beyond the vesicle in which they are contained and/or that vesicles may coalesce allowing the contents of a vesicle to be released by coalescing with a disrupted vesicle. As referred to herein "taken up" signifies that the molecule taken up is wholly contained within the vesicle. The intracellular vesicle is bounded by membranes and may be any such vesicle resulting after endocytosis/phagocytosis, e.g. an endosome, lysosome or phagosome.

As used herein, a "disrupted" compartment refers to destruction of the integrity of the membrane of that compartment either permanently or temporarily, sufficient to allow release of the molecules contained within it.

As defined herein "treatment" (or treating) refers to reducing, alleviating or eliminating one or more symptoms of the bacterial infection which is being treated, relative to the symptoms prior to treatment. Such symptoms may be correlated with the abundance of bacteria present in the treated cells and/or on the treated patient or subject. Treatment in an in vitro method comprises killing, damaging or preventing replication of the bacteria in the cell(s) and may be determined by assessing the abundance of viable bacteria in the cell(s). "Prevention" (or preventing or prophylaxis) refers to delaying or preventing the onset of the symptoms of the bacterial infection. Prevention may be absolute (such that no bacterial infection occurs) or may be effective only in some individuals, or cells, or for a limited amount of time.

As referred to herein a "bacterial infection" is invasion of a cell(s) or bodily tissue by bacteria that proliferate at that site and which may result in injury to that cell or tissue. A cell which is "infected" contains one or more intracellular bacteria capable of survival and potentially replication in that cell. Preferably the bacterial infection is caused by the bacteria described hereinafter, preferably by bacteria selected from the genera *Mycobacterium, Pseudomonas, Escherichia* and *Staphylococcus*. Also preferred are intracellular bacterial infections by bacteria selected from the genera *Coxiella, Listeria, Francisella* and *Rickettsia*. In a preferred aspect the bacteria does not produce spores. In a further preferred aspect the bacteria which appear intracelullarly are not also present in a biofilm, though in an alternative option they may so appear.

Preferably, in the methods and uses of the invention, the infection is present in cells of, or associated with, bones, blood, the heart, urinary tract, lung, skin or mucosal surfaces. Thus in one aspect, bacterial infections to be treated include osteomyelitis, bacteremia, tuberculosis, Q-fever and endocarditis and (sub)cutaneous skin or mucosal infections/damages such as chronic wounds, ulcers, abscesses and diabetic foot infection as well as oral and nasal infections such as chronic rhinosinusitis and periodontitis.

In a further preferred aspect, the method or use is for treating a biomaterial-associated infection and the cells to be treated are present on, or adjacent to, biomaterial introduced into the subject. For example, the biomaterial-associated infection may be peri-implantitis (infection around dental implants). An intracellular bacterial infection which remains after a biomaterial has been removed from a subject may also be treated. Infection is a frequent complication of the use of biomaterials such as medical devices despite all due care being taken in their insertion and care. Infections with *Staphylococcus aureus* and *Staphylococcus epidermidis* are particularly prevalent. Infections of biomaterials are very resistant to treatment. Prolonged application of antibodies is needed, and in many cases the biomaterial has to be removed which can have dramatic consequences for the patient/subject, e.g. when permanent implants such as prosthetic joints or heart valves are involved. Even after removal, eradication of bacteria residing in the infected area requires prolonged antibiotic treatment (which can be up to 6 months). Research has shown that bacteria persist in tissue surrounding a biomaterial. Macrophages have been implicated as the host of the intracellular bacteria and maintain a reservoir of bacteria for repeat infections. The methods and uses of the invention allow this "hiding" bacteria to be targeted.

As referred to herein a "biomaterial" is an artificial material or device which may be introduced into a subject for curative purposes. Such biomaterials include a medical device, instrument, implement or equipment, a prosthetic or material, tissue or wound dressing (e.g. for orthopaedic, cardiovascular, urinary tract, surgical, gynaecological or dental purposes). Medical devices include pacemakers, heart valves and stents, medical implements include catheters, prosthetics or material include artificial joints, implants (including breast and dental implants), bone fixation plates and screws and scaffold material (e.g. surgical meshes). Wound dressings include plasters and bandages as well as cements, glues or matrices which may be used for wound repair. As discussed hereinafter the antibacterial agent and/or the photosensitizing agent may be provided on or within (e.g. embedded within or impregnated in) the biomaterial.

An "intracellular" bacterial infection refers to an infection in which the bacteria are taken up into the cell and are able to survive and replicate in that cell. The bacteria may additionally exist and replicate outside the cell. Such intracellular bacteria may be present at any location within the cell, e.g. within the cytosol or in a membrane-contained subcompartment such as a lysosome, endosome or phagosome. Examples of intracellular bacterial infections which may be treated or prevented according to the invention include infections by *Mycobacterium* (e.g. *M. tuberculosis*), *Pseudomonas* (e.g. *P. aeruginosa*), *Escherichia* (e.g. *E. coli*), and *Staphylococcus* (e.g. *S. aureus* or *S. epidermidis*). In one particular embodiment the subject to be treated is a cow and the bacterial infection is *S. aureus* mastitis. Other intracellular bacterial infections of interest include infections by *Listeria* (e.g. *Listeria monocytogenes*), *Francisella* (e.g. *Francisella tularensis*), *Coxiella* (e.g. *C. burnetti*) and *Rickettsia*.

In the context of the present invention the "cell" or "cells" may be in a culture or in a tissue, organ or body. Thus the cell may be provided in vitro, ex vivo or may be within a subject or organism, e.g. an in vivo cell. The term "cell" includes all eukaryotic cells (including insect cells and fungal cells). Representative "cells" thus include all types of mammalian and non-mammalian animal cells, plant cells, insect cells, fungal cells and protozoa. Preferably, however, the cells are eukaryotic, e.g. from a mammal, reptile, bird, insect or fish. Preferably the cell is from a mammal, particularly a primate, domestic animal, livestock or laboratory animal. Especially preferably the cells are mammalian, for example cells from monkeys, cats, dogs, horses, donkeys, sheep, pigs, goats, cows, mice, rats, rabbits, guinea pigs, but most preferably from humans.

The cells which are infected may be phagocytic cells such as macrophages, dendritic cells or neutrophils or may be "non-professional" phagocytic cells such as epithelial cells, endothelial cells, keratinocytes, osteoblasts and fibroblasts.

An "antibacterial agent" is an entity (e.g. a molecule) which has the ability to kill, damage or prevent the replication of selected bacteria under in vitro conditions, e.g. when in direct contact under culture conditions. The bacteria are preferably as described herein. (As referred to herein bacteria are referred to in both the singular and plural. In particular they are referred to in the singular when defining the type of bacteria to be targeted (i.e. the type, e.g. species, applicable to each bacterium) and in the plural when referring to the treatment to which they may be subjected (i.e. treatment of multiple microorganisms).) In particular, the antibacterial activity is assessed by determining the MIC or MBC value against one or more bacteria, e.g. against a *Staphylococcus* bacteria. Antibacterial activity may be determined by reference to the MIC value, minimum inhibition concentration (MIC), which is defined as the minimum concentration of an antimicrobial agent that inhibits visible growth of micro-organisms in specified liquid media after overnight incubation. Alternatively antibacterial activity may be determined by the minimum bactericidal concentration (MBC) which is the minimum concentration that kills 99.9% of the bacteria during this incubation period. Preferably antibacterial agents have a MIC value of less than 50 µg/ml, preferably less than 30 µg/ml, especially preferably less than 10, 5 or 1 µg/ml, preferably against a bacteria as described herein.

In a preferred aspect the antibacterial agent is an antibiotic, i.e. selectively treats specific bacteria (genera or species).

The antibacterial agent may be selected from aminoglycosides (e.g. amikacin, gentamicin, kanamycin, neomycin, netilmicin, tobramycin, paromomycin, streptomycin or spectinomycin); ansamycins (e.g. geldanamycin, herbimycin or rifaximin); carbacephems (e.g. loracarbef); carbapenems (e.g. ertapenem, doripenem, imipenem, meropenem); cephalosporins (e.g. cefadroxil, cefazolin, cefalexin, cefaclor, cefprozil, cefuroxime, cefixime, cefdinir, cefditoren, cefoperazone, cefotaxime, cefpodoxime, ceftazidime, ceftiaxone, cefepime, ceftaroline fosamil or ceftobiprole), glycopeptides (e.g. teicoplanin, vancomycin, telavancin, dalbavancin or oritavancin); lincosamides (e.g. clindamycin or lincomycin); lipopeptides (e.g. daptomycin); macrolides (e.g. azithromycin, clarithromycin, erythromycin, roxithromycin, telithromycin, fidaxomicin or spiramycin); monobactams (e.g. aztreonam); nitrofurans (e.g. furzolidone or nitrofurantoin); oxazolidinones (e.g. linezolid, posizolid, radezolid or torezolid); penicillins (e.g. amoxicillin, ampicillin, azlocillin, dicloxacillin, flucloxacillin, mezlocillin, methicillin, nafcillin, oxacillin, penicillin (G or V), piperacillin, temocillin or ticarcillin); polypeptides (bacitracin, colistin, polymyxin B); quinolones (e.g. ciprofloxacin, enfloxacin, gatifloxacin, gemifloxacin, levofloxacin, lomefloxacin, moxifloxacin, nalidixic acid, norfloxacin, ofloxacin, trovafloxacin, grepafloxacin, sparfloxacin or temafloxacin); sulfonamides (e.g. mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole or sulfonamidochrysoidine); tetracyclines (e.g. demeclocycline, doxycycline, minocycline, oxytetracycline or tetracycline); and other antibacterial agents such as clofazimine, dapsone, capreomycin, cycloserine, ethambutol, ethionamide, isoniazid, pyrazinamide, rifampicin, rifabutin, rifapentine, streptomycin, arsphenamine, choramphenicol, fosfomycin, fusidic acid, metronidazole, mupirocin, platensimycin, quinupristin/dalfopristin, thiamphenicol, tigecycline, tinidazole or trimethoprim; or any combination thereof.

In a preferred feature, the antibacterial agent is an aminoglycoside (preferably gentamicin), a glycopeptide (preferably vancomycin) or a macrolide (preferably as described hereinbefore). In the methods and uses described herein optionally more than one antibacterial agent may be used, e.g. gentamicin and rifampicin. When more than one agent (e.g. two or three agents) are used, they can be used (e.g. administered) simultaneously, sequentially or separately as described herein for the methods and uses of the invention.

A "photosensitizing agent" as referred to herein is a compound that is capable of translating the energy of absorbed light into chemical reactions when the agent is activated on illumination at an appropriate wavelength and intensity to generate an activated species. The highly reactive end products of these processes can result in cyto- and vascular toxicity. Conveniently such a photosensitizing agent may be one which localises to intracellular compartments, particularly endosomes, phagosomes or lysosomes.

Photosensitizing agents may exert their effects by a variety of mechanisms, directly or indirectly. Thus for example, certain photosensitizing agents become directly toxic when activated by light, whereas others act to generate toxic species, e.g. oxidising agents such as singlet oxygen or other reactive oxygen species, which are extremely destructive to cellular material and biomolecules such as lipids, proteins and nucleic acids.

A range of such photosensitizing agents are known in the art and are described in the literature, including in WO96/07432, which is incorporated herein by reference, and may be used in methods and uses of the invention. There are many known photosensitizing agents, including porphyrins, phthalocyanines and chlorins, (Berg et al., 1997, J. Photochemistry and Photobiology, 65, p403-409, incorporated herein by reference). Other photosensitizing agents include bacteriochlorins.

Porphyrins are the most extensively studied photosensitizing agents. Their molecular structure includes four pyrrole rings linked together via methine bridges. They are natural compounds which are often capable of forming metal-complexes. For example in the case of the oxygen transport protein hemoglobin, an iron atom is introduced into the porphyrin core of heme B.

Chlorins are large heterocyclic aromatic rings consisting, at the core, of three pyrroles and one pyrroline coupled through four methine linkages. Unlike porphyrin, a chlorin is therefore largely aromatic, but not aromatic through the entire circumference of the ring.

Particularly preferred are photosensitizing agents which locate to endosomes, phagosomes or lysosomes of cells. Thus, the photosensitizing agent is preferably an agent which is taken up into the internal compartments of lysosomes, phagosomes or endosomes. Preferably the photosensitizing agent is taken up into intracellular compartments by endocytosis or phagocytosis. Preferred photosensitizing agents are amphiphilic photosensitizers (e.g. disulphonated photosensitizing agents) such as amphiphilic phthalocyanines, porphyrins, chlorins, and/or bacteriochlorins, and in particular include sulfonated (preferably disulfonated) meso-tetraphenyl chlorins, porphyrins, phthalocyanines and bacteriochlorins. In a preferred aspect, the photosensitizing agent is selected from a porphyrin, phthalocyanine, purpurin, chlorin, benzoporphyrin, lysomotropic weak base, naphthalocyanine, cationic dye, tetracycline, 5-aminolevulinic acid and/or esters thereof, or a derivative of any of said agents, preferably $TPPS_4$, $TPPS_{2a}$, $AlPcS_{2a}$, $TPCS_{2a}$, 5-aminolevulinic acid or esters of 5-aminolevulinic acids, or pharmaceutically acceptable salts thereof. Particularly preferred are $TPPS_{2a}$ (tetraphenylporphine disulfonate), $AlPcS_{2a}$ (aluminium phthalocyanine disulfonate), $TPCS_{2a}$ (tetraphenyl chlorin disulfonate) and $TPBS_{2a}$ (tetraphenyl bacteriochlorin disulfonate), or pharmaceutically acceptable salts thereof. Preferably the photosensitizing agent is $TPCS_{2a}$ (Disulfonated tetraphenyl chlorin, e.g. Amphinex®).

As used herein "and/or" refers to one or both (or more) of the recited options being present, e.g. A and/or B includes the options i) A, ii) B or iii) A and B.

The structures of preferred photosensitizing agents are provided below:

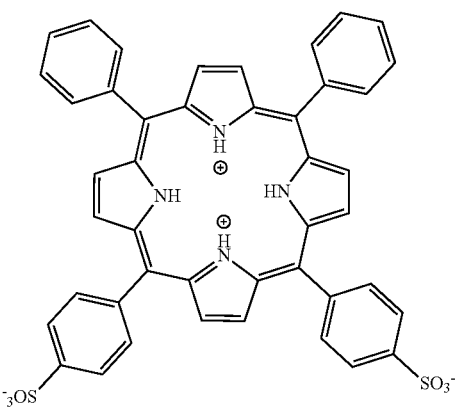

$TPPS_{2a}$(Tetraphenyl prophyrin disulphonate)

-continued

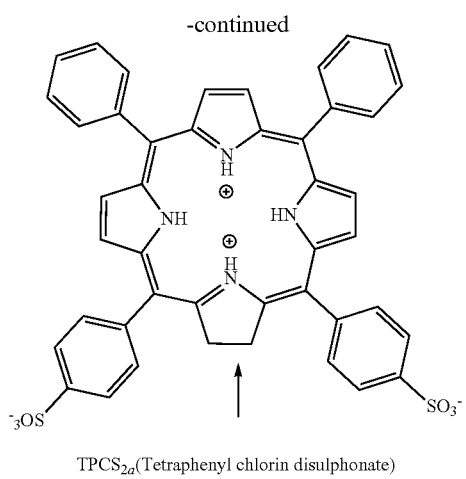

TPCS$_{2a}$(Tetraphenyl chlorin disulphonate)

The arrow indicates the structural difference between the two molecules.

Optionally, the photosensitizing agent may be attached to or associated with or conjugated to one or more carrier molecules or targeting molecules which can act to facilitate or increase the uptake of the photosensitizing agent. Thus the photosensitizing agent may be linked to a carrier. For example, the photosensitizing agent may be provided in the form of a conjugate, e.g. a chitosan-based conjugate, for example a conjugate disclosed in WO2013/189663, which is hereby incorporated by reference.

As used herein "contacting" refers to bringing the cell(s) and the various components (or agents) used in the method into physical contact with one another under conditions appropriate for internalization into the cells, e.g. preferably at 37° C. in an appropriate nutritional medium, e.g. from 25-39° C., or in vivo. The cell may be contacted with the photosensitizing agent and the antibacterial agent used in the method as defined herein sequentially or simultaneously. Conveniently the components are contacted with the cell(s) simultaneously and preferably are applied to the cell(s) together as described in more detail hereinafter. The different components may be taken up by the cell(s) into the same or different intracellular compartments (e.g. they may be co-translocated). However, in an alternative embodiment the components are not applied together, i.e. are applied at a different time and/or by a different administration route.

The cells are then exposed to light of suitable wavelengths to activate the photosensitizing compound which in turn leads to the disruption of the intracellular compartment membranes.

WO 02/44396 (which is incorporated herein by reference) describes a method in which the order of the steps in the method may be arranged such that for example the photosensitizing agent is contacted with the cells and activated by irradiation before the molecule to be internalised (in this case the antibacterial agent) is brought into contact with the cells. This method takes advantage of the fact that it is not necessary for the molecule to be internalised to be present in the same cellular subcompartment as the photosensitizing agent at the time of irradiation.

Thus in one embodiment, said photosensitizing agent and said antibacterial agent as defined herein are applied to the cell together, or separately relative to one another. Irradiation is then performed at a time when the photosensitizing agent and the antibacterial agent appear in the same intracellular compartment. This is referred to as a "light after" method.

In an alternative embodiment, said method can be performed by contacting said cell with the photosensitizing agent first, followed by contact with the antibacterial agent to be used as defined herein, and irradiation is performed after uptake of the photosensitizing agent into an intracellular compartment, but prior to the cellular uptake of the antibacterial agent into an intracellular compartment containing said photosensitizing agent (e.g. they may be present in a different intracellular compartment at the time of light exposure), preferably prior to cellular uptake into any intracellular compartment, e.g. prior to any cellular uptake. Thus for example the photosensitizing agent may be administered followed by irradiation and then administration of the antibacterial agent. This is the so-called "light before" method.

"Internalisation" as used herein, refers to the intracellular, e.g. cytosolic, delivery of molecules. In the present case "internalisation" may include the step of release of molecules from intracellular/membrane bound compartments into the cytosol of the cells.

As used herein, "cellular uptake" or "translocation" refers to one of the steps of internalisation in which molecules external to the cell membrane are taken into the cell such that they are found interior to the outer lying cell membrane, e.g. by endocytosis, phagocytosis or other appropriate uptake mechanisms, for example into or associated with intracellular membrane-restricted compartments, for example the endoplasmic reticulum, Golgi body, lysosomes, endosomes, phagosomes etc.

Generally the method is performed on a cell(s) that is already infected with bacteria. However, the method may also be performed on a cell(s) that is not yet infected with bacteria or a cell(s) which is in the process of being infected with bacteria (in which case the method is a prevention method). When the cell(s) is in the process of being infected, bacteria may be taken up with the photosensitizing agent and/or antibacterial agent during the PCI method. When the cell(s) has not yet been infected, the cell(s) may be a cell(s) which is identified to be at risk of infection (e.g. at a site where intracellular infection is likely, e.g. biomaterial-associated infection when a device is to be used). In this case the method may be performed at the site of interest immediately before placement of the device.

The step of contacting the cells with the different agents may be carried out in any convenient or desired way. Thus, if the contacting step is to be carried out in vitro the cells may conveniently be maintained in an aqueous medium, such as for example appropriate cell culture medium, and at the appropriate time point the various agents can simply be added to the medium under appropriate conditions, for example at an appropriate concentration and for an appropriate length of time. For example, the cells may be contacted with the agents in the presence of serum-free medium, or with serum-containing medium.

The comments below discuss the application of the different agents to the cells separately. As discussed above however, these agents may be applied to cells together, separately, simultaneously or sequentially. As referred to herein, the application of the agents used in the methods and uses of the invention may be to cells in vitro or in vivo. In the latter case, the application may be via direct (i.e. localized or topical) or indirect (i.e. systemic or non-localized) administration as described in more detail hereinbelow.

The photosensitizing agent is brought into contact with the cells at an appropriate concentration and for an appropriate length of time which can easily be determined by a skilled person using routine techniques, and will depend on such factors as the particular photosensitizing agent used, the mode of administration, the course of treatment, the age and weight of the patient/subject, the medical indication, the body or body area to be treated and may be varied or adjusted according to choice. The concentration of the photosensitizing agent is conveniently such that once taken up into the cell, e.g. into, or associated with, one or more of its intracellular compartments and activated by irradiation, one or more cell structures are disrupted e.g. one or more intracellular compartments are lysed or disrupted.

For example, photosensitizing agents as described herein may be used at a concentration of for example 0.1 to 50 µg/ml. For in vitro use the range can be much broader, e.g. 0.0005-500 µg/ml. For in vivo human treatments the photosensitizing agent may be used in the range 0.05-20 mg/kg body weight when administered systemically. Alternatively, a range of 0.005-20 mg/kg body weight may be used for systemic administration. For systemic delivery the total dose provided may be in the order of 1-5000 µg, for example 10-2500, 25-1000, 50-500, 10-300, 25-200, or 100-300 µg. Preferably the dose is selected from 100 µg, 150 µg, 200 µg and 250 µg. Preferably the dose is 75-125 µg, e.g. 100 µg. If administered locally, for example by topical, intradermal or subcutaneous administration, the dose may be in the region of 0.001-500 µg or 0.1-500 µg, for example 0.001-0.1, 0.0025-1, 0.01-50, 0.0025-250, 1-250, 2.5-100, 2.5-40, 5-50, 1-30 or 10-30 µg. For local delivery, preferably the dose is selected from 10 µg, 15 µg, 20 µg and 25 µg. Preferably the dose is 7.5-12.5 µg, e.g. 10 µg. The doses provided are for a human of average weight (i.e. 70 kg). For intradermal injection the photosensitizer dose may be dissolved in 100 µl-1 ml, i.e. the concentration may be in the range of 0.01-50000 µg/ml or 1-50000 µg/ml. In smaller animals the concentration range may be different and can be adjusted accordingly though when administered locally, little variation in dosing is necessary for different animals.

The concentration of the antibacterial agent as defined herein will also depend on the particular molecule which is to be used, the mode of administration, the course of treatment, the age and weight of the patient/subject, the medical indication, the body or body area to be treated and may be varied or adjusted according to choice.

For example, antibacterial agents as described herein may be used at a concentration of for example 0.01 to 50 µg/ml. For in vitro use the range can be much broader, e.g. 0.0005-500 µg/ml. For in vivo human treatments the antibacterial agent may be used in the range 0.05-100 mg/kg body weight when administered systemically. Alternatively, a range of 0.005-100 mg/kg body weight, preferably 0.1 to 50 mg/kg, may be used for systemic administration. If administered locally, for example by topical, intradermal or subcutaneous administration, the dose may be in the region of 1-50000 µg, for example 10-25000, 25-10000, 50-5000, 10-3000 or 100-3000 µg. Preferably the dose is selected from 1 mg, 1.5 mg, 2 mg and 2.5 mg. Preferably the dose is 0.75-1.25 mg, e.g. 1 mg. The doses provided are for a human of average weight (i.e. 70 kg). For intradermal injection the antibacterial agent dose may be dissolved in 100 µl-1 ml, i.e. the concentration may be in the range of 1-50000 µg/ml. In smaller animals the concentration range may be different and can be adjusted accordingly though when administered locally, little variation in dosing is necessary for different animals.

In most cases the photosensitizing agent and the antibacterial agent are administered together, but this may be varied. Thus different times or modes or sites of administration (or contact with the cell) are contemplated for each of the different components and such methods are encompassed within the scope of the invention.

In one embodiment the antibacterial agent as defined herein is administered separately from the photosensitizing agent, for example in a separate formulation, or systemically, e.g. via oral administration. Thus, in one embodiment the antibacterial agent or the photosensitizing agent may be administered prior to administration of the photosensitizer or antibacterial agent, respectively, for example up to 24 or 48 hours before. Preferably the separate administrations are separated by less than 48, 24, 12, 8, 4 or 2 hours. By way of example, the photosensitizer may be administered first (e.g. locally to avoid skin photosensitivity) and the antibacterial agent may then be administered systemically.

The contact between the cell(s) and the photosensitizing agent and/or antibacterial agent as defined herein is conveniently from 15 minutes to 24 (or 48) hours (e.g. 15 or 30 minutes to 4 hours, e.g. 1-2 hours). The contacting may be simultaneous or sequential or the timing of contacting with the separate components may overlap. The contacting step refers to the total contact time of the cell(s) with the agent in question and that contacting time may be made up of a number of discrete separate contacting steps. The agent may be removed from contact with the cell(s) for a period of time before the irradiation step. In in vitro methods, in a preferred aspect, the contacting step for each agent may be 15 (or 30) to 120 minutes. In vivo a similar contact time may be used, but the cells may not be contacted with the agents immediately after administration (e.g. where systemic administration is used) and in such case the agents will need to be administered sufficiently before illumination so that the agents reach the target cells and have contact with those cells for the required contact time, as discussed hereinbelow in more detail.

In a preferred embodiment the initial incubation of the cell is with the photosensitizing agent. In one embodiment the time between the administration of the photosensitizing agent and the antibacterial agent is a matter of hours. For example, the photosensitizing agent may be applied 16 to 20 (or 40 to 44) hours, e.g. 18 hours, before illumination, and the antibacterial agent may be applied 1 to 3 hours, e.g. 2 hours before illumination. Thus, the time between the administration of the photosensitizing agent and the antibacterial agent may be in the range of 15 to 23 (or 47) hours. This timing applies regardless of which agent is administered first.

Conveniently the cell(s) may be placed into photosensitizer/antibacterial agent-free medium after the contact with the photosensitizer/antibacterial agent and before irradiation, e.g. for 30 minutes to 4 hours, e.g. from 1.5 to 2.5 hours, depending on the timing of the incubation with the photosensitizer and antibacterial agent.

In vivo an appropriate method and time of incubation by which the various agents are brought into contact with the target cells will be dependent on factors such as the mode of administration and the type of agents which are used. For example, if the agents are injected into a tissue or organ which is to be treated/irradiated, or applied topically, the cells near the injection or application point will come into contact with and hence tend to take up the agents more rapidly than the cells located at a greater distance from the injection or application point, which are likely to come into contact with the agents at a later time point and lower concentration. Conveniently a time of 6-24 (or 6-48) hours may be used.

In addition, agents administered by intravenous injection or orally may take some time to arrive at the target cells and it may thus take longer post-administration e.g. several days, in order for a sufficient or optimal amount of the agents to accumulate in a target cell or tissue. The time of administration required for individual cells in vivo is thus likely to vary depending on these and other parameters.

Nevertheless, although the situation in vivo is more complicated than in vitro, the underlying concept of the present invention is still the same, i.e. the time at which the molecules come into contact with the target (i.e. infected) cells must be such that before irradiation occurs an appropriate amount of the photosensitizing agent has been taken up by the target cells and either: (i) before or during irradiation the antibacterial agent has either been taken up, or will be taken up after sufficient contact with the target cells, into the cell, for example into the same or different intracellular compartments relative to the photosensitizing agent or (ii) after irradiation the antibacterial agent is in contact with the cells for a period of time sufficient to allow its uptake into the cells.

For administration of agents described herein in vivo, any mode of administration common or standard in the art may be used, e.g. oral, parenteral (e.g. intramuscular, transdermal, subcutaneous, percutaneous, intraperitoneal, intrathecal or intravenous), intestinal, buccal, rectal or topical, both to internal and external body surfaces etc. For in vivo use, the invention can be used in relation to any tissue which contains cells to which the photosensitizing agent containing compound or the antibacterial agent is localized, including body fluid locations, as well as solid tissues. All tissues can be treated as long as the photosensitizer is taken up by the target cells, and the light can be properly delivered. Preferred modes of administration are intradermal, subcutaneous or topical administration or injection. Preferably administration is topical (also referred to herein as local administration).

Administration may be by application of the required agents to the cell(s) at the time of the treatment/prevention method (e.g. administration to the patient/subject) or one or more of the required agents may be provided in a formulation which allows slow or controlled (on demand) release, which may then be followed with the treatment/prevention step. For example, the antibacterial agent and/or the photosensitizing agent may be provided on or within (e.g. embedded within or impregnated in) a biomaterial to be used on or in a patient/subject. Such agents may be released slowly with time or released on demand and the treatment/prevention step initiated by irradiation (optionally with administration of one of the required agents if not present in/on the biomaterial). Conveniently in assessing timings and doses such administration is considered local administration.

To achieve the desired outcome, i.e. treatment or prevention of bacterial infection, the methods or parts thereof may be repeated. Thus, the method in its entirety may be performed multiple times (e.g. 2, 3 or more times) after an appropriate interval or parts of the method may be repeated, e.g. further administration of the antibacterial agent and/or photosensitizing agent as defined herein or additional irradiation steps. For example, the method or part of the method may be performed again a matter of days, e.g. between 5 and 60 days (for example 7, 14, 15, 21, 22, 42 or 51 days), e.g. 7 to 20 days, preferably 14 days, or weeks, e.g. between 1 and 5 weeks (for example, 1, 2, 3 or 4 weeks) after it was first performed. All or part of the method may be repeated multiple times at appropriate intervals of time, e.g. every two weeks or 14 days. In a preferred embodiment the method is repeated at least once. In another embodiment the method is repeated twice.

"Irradiation" to activate the photosensitizing agent refers to the administration of light directly or indirectly as described hereinafter. Thus the cell(s) (which may be present in a subject) may be illuminated with a light source for example directly (e.g. on single cells in vitro) or indirectly, e.g. in vivo when the cells are below the surface of the skin or are in the form of a layer of cells not all of which are directly illuminated, i.e. without the screen of other cells. Illumination of the cell or subject may occur approximately 15 minutes to 24 (or 48) hours after administration of the various components for use in the method as defined herein. In in vitro methods, illumination may occur from, for example 15 to 120 minutes after administration, whereas in in vivo methods a longer time after administration may be required if contact time with the target cells within the subject is not immediate (depending on the route of administration), e.g. from 15 minutes to 24 (or 48) hours after administration.

The light irradiation step to activate the photosensitizing agent may take place according to techniques and procedures well known in the art. The dose, wavelength and duration of the illumination must be sufficient to activate the photosensitizing agent, i.e. to generate reactive species.

The wavelength of light to be used is selected according to the photosensitizing agent to be used. Suitable artificial light sources are well known in the art, e.g. using blue (400-475 nm) or red (620-750 nm) wavelength light. For $TPCS_{2a}$, for example, a wavelength of between 400 and 500 nm, more preferably between 400 and 450 nm, e.g. from 430-440 nm, and even more preferably approximately 435 nm, or 435 nm may be used. Where appropriate the photosensitizer, e.g. a porphyrin or chlorin, may be activated by green light, for example the KillerRed (Evrogen, Moscow, Russia) photosensitizer may be activated by green light.

Suitable light sources are well known in the art, for example the LumiSource® lamp of PCI Biotech AS. Alternatively, an LED-based illumination device which has an adjustable output power of up to 60 mW and an emission spectra of 430-435 nm may be used. For red light, a suitable source of illumination is the PCI Biotech AS 652 nm laser system SN576003 diode laser, although any suitable red light source may be used.

The time for which the cells are exposed to light in the methods of the present invention may vary. The efficiency of the internalisation of a molecule into the cytosol increases with increased exposure to light to a maximum beyond which cell damage and hence cell death increases.

A preferred length of time for the irradiation step depends on factors such as the target, the photosensitizer, the amount of the photosensitizer accumulated in the target cells or tissue and the overlap between the absorption spectrum of the photosensitizer and the emission spectrum of the light source. Generally, the length of time for the irradiation step is in the order of seconds to minutes or up to several hours (even up to 12 hours), e.g. preferably up to 60 minutes e.g. from 0.25 or 1 to 60 minutes, e.g. from 5 to 60 minutes, preferably for 10 to 20 minutes, preferably for 15 minutes. Shorter irradiation times may also be used, for example 1 to 60 seconds, e.g. 10-50, 20-40 or 25-35 seconds, e.g. when higher doses of photosensitizing agent are used.

Appropriate light doses can be selected by a person skilled in the art and again will depend on the photosensitizer used and the amount of photosensitizer accumulated in the target cell(s) or tissues. The light doses are usually lower when photosensitizers with higher extinction coefficients (e.g. in the red area, or blue area if blue light is used, depending on the photosensitizer used) of the visible spectrum are used. For example, a light dose in the range of 0.24-7.2 $J/cm^2$ at a fluence range of 0.05-20 $mW/cm^2$, e.g. 2.0 $mW/cm^2$, may be used when an LED-based illumination device which has an adjustable output power of up to 60 mW and an emission spectra of 430-435 nm is employed. Alternatively, e.g. if the LumiSource® lamp is employed a light dose in the range of 0.1-6 $J/cm^2$ at a fluence range of 0.1-20 (e.g. 13 as provided by Lumisource®) $mW/cm^2$ is appropriate. For red light, a light dose of 0.03-1 $J/cm^2$, e.g. 0.3 $J/cm^2$, at a fluence range of 0.1-5 $mW/cm^2$, e.g. 0.81 $mW/cm^2$, may be used.

Furthermore, if cell viability is to be maintained, the generation of excessive levels of toxic species is to be avoided and the relevant parameters may be adjusted accordingly.

The methods of the invention may inevitably give rise to some cell damage by virtue of the photochemical treatment i.e. by photodynamic therapy effects through the generation of toxic species on activation of the photosensitizing agent. Depending on the proposed use, this cell death may not be of consequence and may indeed be advantageous to remove some bacteria-infected cells. In most embodiments, however, cell death is avoided, e.g. to allow the antibacterial effects to occur. The methods of the invention may be modified such that the fraction or proportion of the surviving cells is regulated by selecting the light dose in relation to the concentration or dose of the photosensitizing agent. Again, such techniques are known in the art.

Preferably, substantially all of the cells, or a significant majority (e.g. at least 75%, more preferably at least 80, 85, 90 or 95% of the cells) are not killed (of those subject to the treatment). In vitro cell viability following PCI treatment can be measured by standard techniques known in the art such as the MTS test. In vivo cell death of one or more cell types may be assessed within a 1 cm radius of the point of administration (or at a certain depth of tissue), e.g. by microscopy. As cell death may not occur instantly, the % cell death refers to the percent of cells which remain viable within a few hours of irradiation (e.g. up to 4 hours after irradiation) but preferably refers to the % viable cells 4 or more hours after irradiation.

PCI allows the antibacterial agent to be released into the cytosol of the cell(s). The agent may then interact with the bacteria to kill or damage the bacteria or to prevent its replication.

"Kill" refers to destruction of a bacteria to the extent that no further replication can take place. "Damage" refers to affecting the bacteria's ability to function normally, such that it may die or be unable to replicate. "Preventing replication" refers to prevention of the replication of the bacteria partially or completely, e.g. according to the percentages described hereinafter. Preferably a method, treatment or use described herein results in the death or damage of at least 25, 50, 75 or 90% of the bacteria to which the treatment is applied or prevents replication such that a bacterial infection is prevented or reduced, e.g. by at least 30, 40, 50, 60, 70, 80 or 90% relative to a control to which the treatment is not applied.

The method may be performed in vivo, in vitro or ex vivo. Preferably the method is used in vivo.

When used in an in vitro method, the method of the invention may alternatively be described as an in vitro method of killing, damaging or preventing the replication of a bacteria in a cell(s), comprising contacting the cell(s) with an antibacterial agent and a photosensitizing agent and irradiating the cell(s) with light of a wavelength effective to activate the photosensitizing agent, wherein the antibacterial agent is released into the cytosol of the cell(s) and kills, damages or prevents the replication of bacteria in said cell(s). Preferred aspects described above also apply to this method.

When used in vivo the "subject" refers to a mammal, reptile, bird, insect or fish. Preferably the subject is a mammal, particularly a primate (preferably a human), domestic or companion animal, livestock or laboratory animal. Thus preferred animals include mice, rats, rabbits, guinea pigs, cats, dogs, monkeys, pigs, cows, goats, sheep and horses.

Conveniently the photosensitizing agent and the antibacterial agent may be provided in a composition. Alternatively they may be in separate solutions or compositions allowing different mechanisms or timings for administration or application. As referred to herein "co-administration" and "co-application" refers to use of both components in the same method rather than simultaneous use (either in terms of timing or in the same composition).

In an alternative recital of the invention, the invention also provides an antibacterial agent as defined hereinbefore, and a photosensitizing agent as defined hereinbefore or a composition comprising an antibacterial agent and a photosensitizing agent as defined hereinafter for use in treating an intracellular bacterial infection in a subject, wherein preferably said use comprises a method as defined hereinbefore. The invention also provides use of an antibacterial agent as defined hereinbefore and/or a photosensitizing agent as defined hereinbefore in the manufacture of a medicament for treating an intracellular bacterial infection in a subject, preferably by a method as defined hereinbefore.

Also provided is use of an antibacterial agent and a photosensitizing agent as an antibacterial, wherein preferably the agents are as described hereinbefore and used in accordance with the method described herein.

The invention further provides a composition comprising an antibacterial agent as defined hereinbefore and a photosensitizing agent as defined hereinbefore, preferably for use in therapy. The composition may be in the form of a pharmaceutical composition comprising in addition one or more pharmaceutically acceptable diluents, carriers or excipients.

These compositions (and products of the invention, described hereinafter) may be formulated in any convenient manner according to techniques and procedures known in the pharmaceutical art, e.g. using one or more pharmaceutically acceptable diluents, carriers or excipients. The compositions may be formulated as slow or delayed release compositions. "Pharmaceutically acceptable" as referred to herein refers to ingredients that are compatible with other ingredients of the compositions (or products) as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule (or components of the composition or product), purpose of treatment, age of patient/subject, mode of administration etc. In connection with the photosensitizing agent, the potency/ability to disrupt membranes on irradiation, should also be taken into account.

The invention also provides a product comprising an antibacterial agent as defined hereinbefore, and a photosensitizing agent as defined hereinbefore as a combined preparation for simultaneous, separate or sequential use in treating an intracellular bacterial infection in a subject.

Finally, the invention provides a kit for use in treating an intracellular bacterial infection in a subject, said kit comprising
- a first container containing a photosensitizing agent as defined hereinbefore; and
- a second container containing an antibacterial agent as defined hereinbefore.

The products and kits of the invention may be used to treat or prevent intracellular bacterial infection as defined hereinbefore.

The methods described in the Examples form further preferred aspects of the invention. All combinations of the preferred features described above are contemplated, particularly as described in the Examples. The invention will now be described by way of non-limiting Examples with reference to the drawings in which:

FIG. 1 shows the effect of PCI on efficacy of gentamicin treatment of intracellular S. epidermidis in Raw 264.7 cells. The initial numbers of intracellular S. epidermidis were determined to be $10^6$ CFU/well immediately after phagocytosis (Uptake). After phagocytosis, cells were treated with 0.25 µg/ml $TPPS_{2a}$ only, with 1, 10 and 30 µg/ml gentamicin (GEN) alone (−), or with the respective gentamicin-$TPPS_{2a}$ combinations (+) for 2 hours. Subsequently the cells were illuminated for 10 or 15 minutes. Non-illuminated cells (no illumination) and non-treated, illuminated cells (No GEN, $TPPS_{2a}$ "−") were used as controls. After treatment, culture medium was replaced with refresh medium containing 1 µg/ml gentamicin to suppress growth of extracellular bacteria, and the cells were incubated overnight. Differences between GEN alone treatment groups and the respective GEN+$TPPS_{2a}$ groups were analyzed using Sidak's multiple comparisons test. Data represent mean ±standard deviation (n=3). ***, $P<0.001$. Two independent experiments were performed, of which one is shown in this figure. The experiments showed highly similar data and statistical significances.

Figure 2:
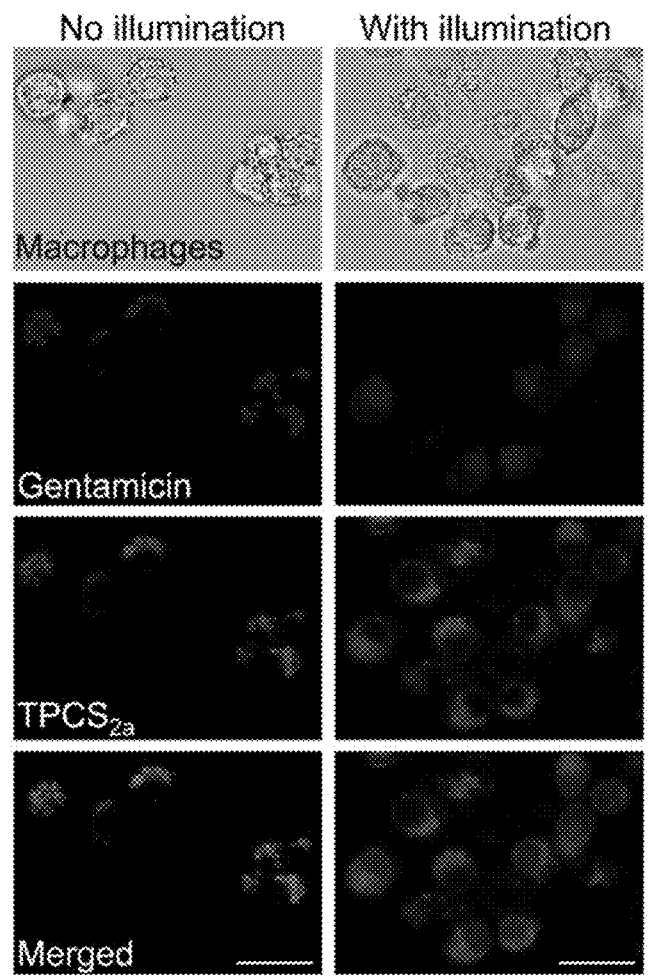

FIG. 2 shows the intracellular distribution of gentamicin and $TPCS_{2a}$ in Raw 264.7 cells with and without illumination of 2 minutes to activate the photosensitizer. Cells were incubated overnight in culture medium containing 10 µg/ml gentamicin (GEN, blue fluorescent) and 1 µg/ml $TPCS_{2a}$ (red fluorescent) before illumination. Intracellular co-localization of gentamicin and $TPCS_{2a}$ appeared in magenta in the merged images. Scale bars=20 µm.

Figure 3:
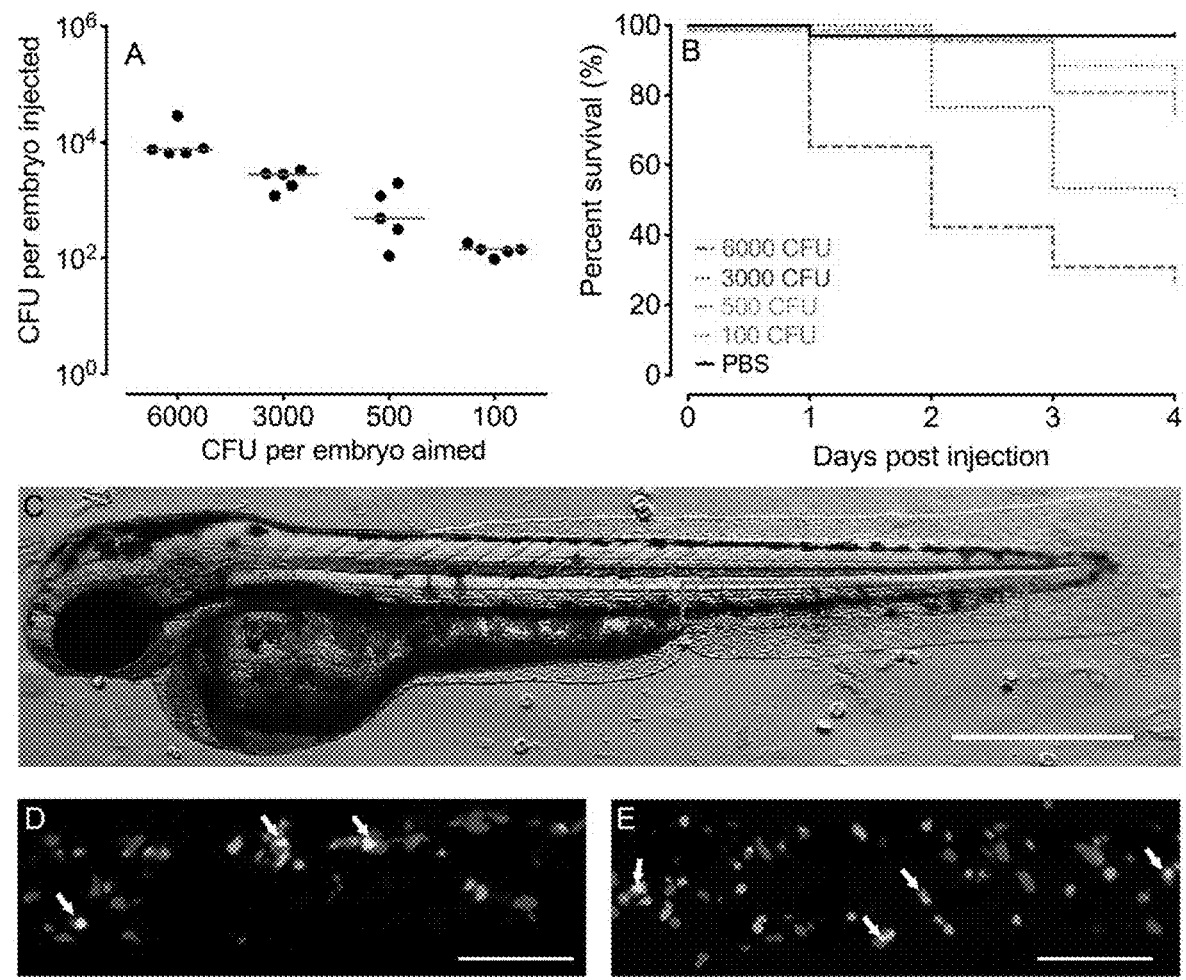

FIG. 3 shows determination of the doses of S. aureus for zebrafish embryo infection and visualization of co-localization of S. aureus and zebrafish phagocytic cells. A) CFU numbers of S. aureus in zebrafish embryos injected with different inocula. Embryos were injected with 1 nl of S. aureus suspension of 100 to 6000 CFU per nl, crushed directly after injection and the resulting suspension was quantitatively cultured to quantify the CFU numbers of injected S. aureus. The lines represent the median CFU numbers. B) The effect of different inocula of S. aureus on survival of zebrafish embryos. PBS injections were used as controls. Initial group sizes ranged from 26 to 38 embryos. C) Co-localization of S. aureus and phagocytic cells of 2 days old zebrafish embryo at 2 hours post injection. The box indicates the area of the recorded co-localization in high magnification shown in D and E. Scale bar=500 µm. The recorded co-localization of green fluorescent protein (GFP)-expressing S. aureus with mCherry protein-expressing macrophages or with DsRed protein-expressing neutrophils are shown in D) and E), respectively. The arrows in D) and E) indicate co-localization. Scale bars=100 µm.

Figure 4:
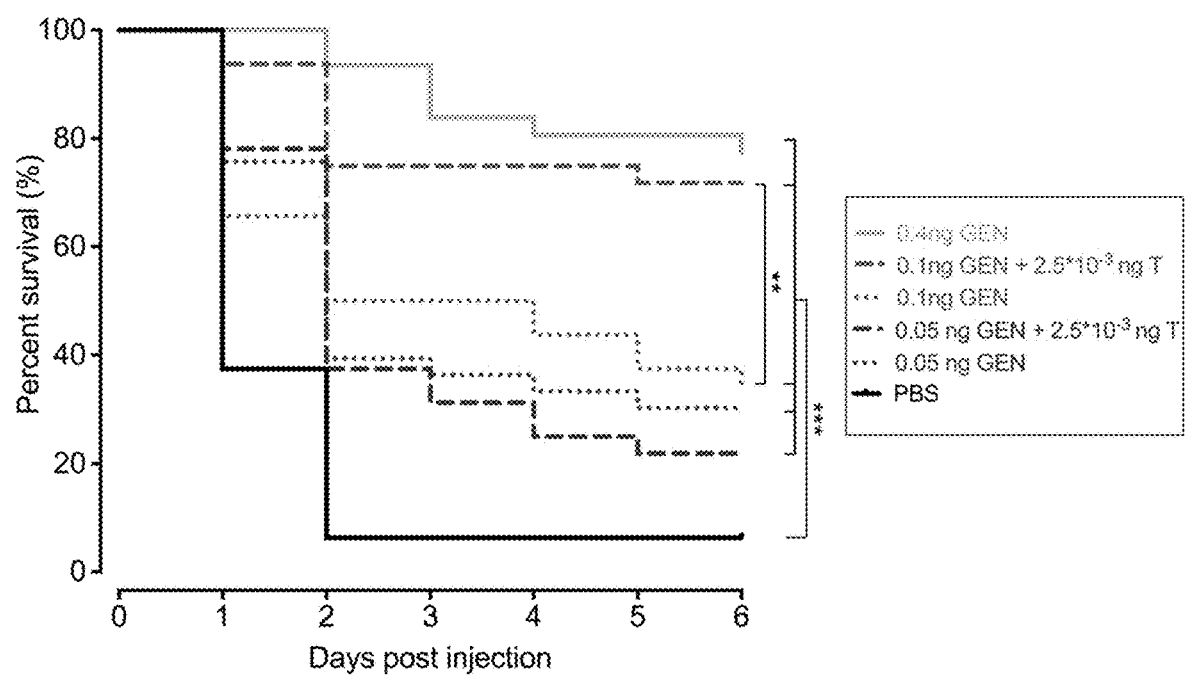

FIG. 4 shows percent survival of S. aureus-infected embryos treated with 0.4 ng gentamicin (GEN), 0.1 and 0.05 ng GEN alone or combined with $2.5*10^{-3}$ ng $TPCS_{2a}$ (T). PBS mock treatment was used as control. Initial group size ranged from 31 to 33 embryos. Differences between survival of gentamicin alone or gentamicin-$TPCS_{2a}$ treatment groups and survival of the PBS mock treatment group, as well as between gentamicin-$TPCS_{2a}$ groups and the respective gentamicin only groups were analyzed using Log-rank test. $p<0.01$. *$p<0.001$.

Figure 5:
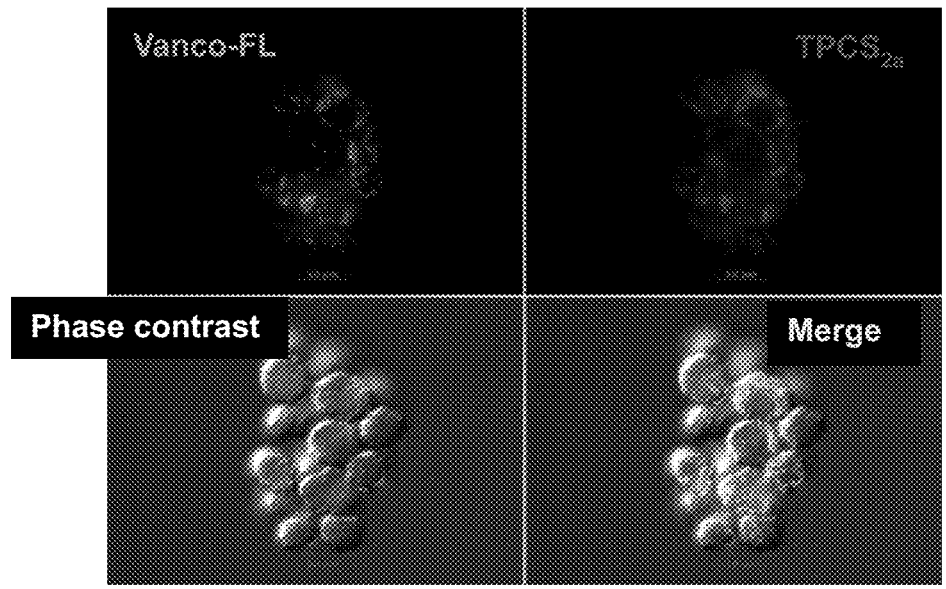
Figure 5:
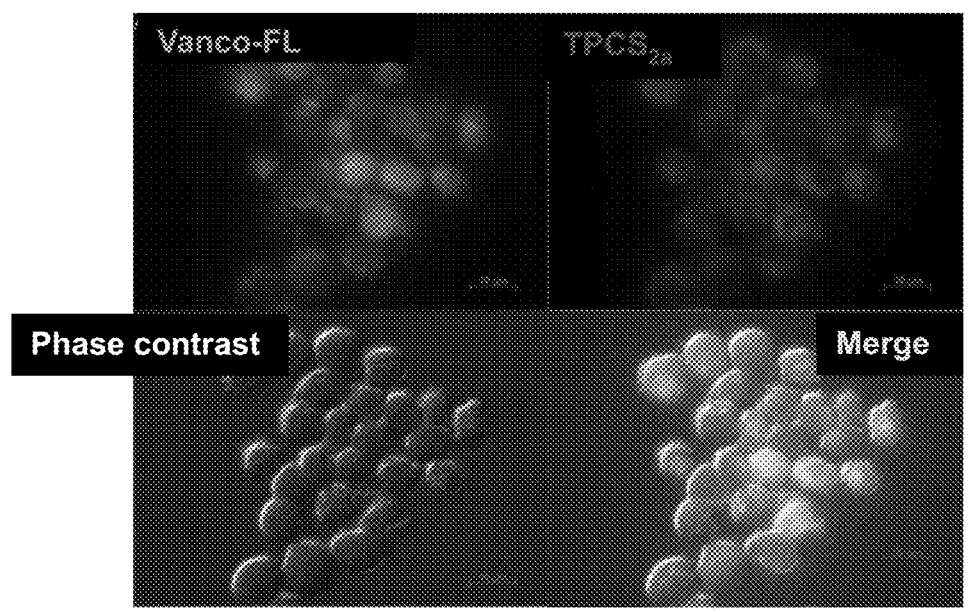

FIG. 5 shows PCI re-localises vancomycin from endocytic vesicles to the cytosol in a macrophage cell line. The intracellular localization of $TPCS_{2a}$ and BODIPY® FL-Vancomycin was analysed by fluorescence microscopy before (A) and after (B) illumination.

Figure 6:
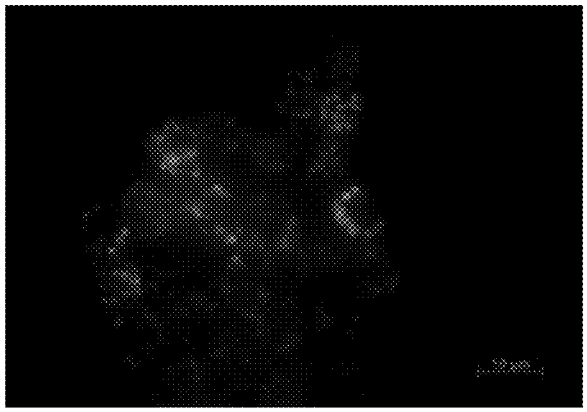
Figure 6:
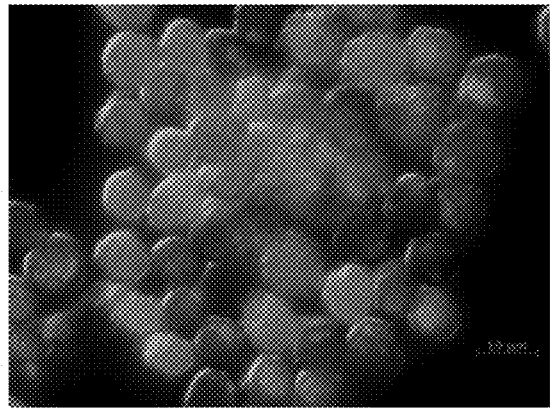

FIG. 6 shows PCI induces disaggregation of vancomycin inside macrophages. RAW 264.7 cells were treated in the same was as cells for FIG. 5. In this experiment the microscopy light excitation time was the same for the samples both before and after PCI, so that the fluorescence intensity can be quantitatively compared.

Figure 7:
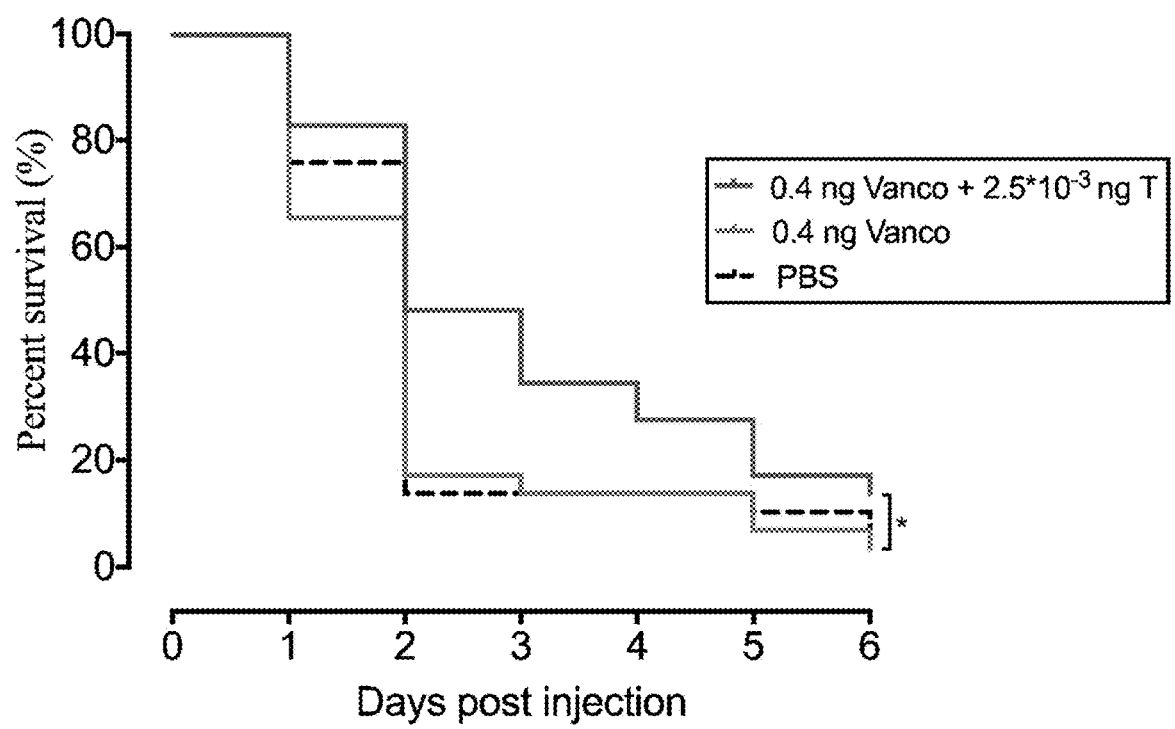

FIG. 7 shows percent survival of S. aureus-infected embryos treated with 0.4 ng vancomycin (Vanco) alone or combined with $2.5*10^{-3}$ ng $TPCS_{2a}$ and illumination (T). PBS mock treatment was used as control. The difference between survival of vancomycin alone group and vancomycin-$TPCS_{2a}$/illumination group was analyzed using Log-rank test, *$p<0.05$.

EXAMPLE 1

Enhanced Antibacterial Efficacy of Gentamicin against Intracellular Staphylococcal Infection by PCI As amphiphilic photosensitizers suited for PCI applications, tetraphenyl porphyrin disulphonate ($TPPS_{2a}$) and its derivative tetraphenyl chlorin disulphonate ($TPCS_{2a}$) have previously been used. $TPPS_{2a}$ and $TPCS_{2a}$ possess very similar physico-chemical properties, but only $TPCS_{2a}$ can be activated by red light. Red light has very good tissue penetration and hence $TPCS_{2a}$ is suitable for broad clinical applications. In the present study, the aim was to assess whether PCI combined with antibiotics (antibacterial agents) could combat intracellular bacterial infection by enhancing cytosolic delivery of antibiotics upon illumination. Gentamicin was selected to study the potential effect of PCI since it has low intracellular antimicrobial efficacy.

Materials and Methods

Bacterial Strains and Inoculum Preparation

S. epidermidis strain O-47 (Riool et al., 2014, supra) was used for in vitro studies with Raw 264.7 mouse macrophages (Raw 264.7 cells) (Xia et al., 2008, Acs Nano, 2(10), p2121-2134). The minimal inhibitory concentration and minimal bactericidal concentration of gentamicin (Centrafarm B.V., The Netherlands) for S. epidermidis in RPMI medium (Gibco, Paisley, UK) supplemented with 5% fetal calf serum (FCS) (designated as RPMI herein) was determined as 0.04 and 0.33 µg/ml, respectively. S. aureus strains ATCC49230 was used for zebrafish embryo infection. S. aureus strain RN4220 containing GFP expression plasmids WWW189 (S. aureus RN4220-GFP) was constructed, following the protocol described earlier (Riool et al., 2014, supra; and Riool et al., 2017, European Cells & Materials, 33, p143-157), and used for in vivo visualization of cell-bacteria interaction in zebrafish embryos. The bacterial suspensions (in PBS or RPMI) with desired concentrations for different experiments were prepared, following the protocol described earlier (Riool et al., 2014, supra; and Riool et al., 2017, supra).

Cytotoxicity of Gentamicin, and Photosensitizer $TPPS_{2a}$ Alone or Combined with *S. epidermidis* for Raw 264.7 Cells Raw 264.7 cells were seeded in a 96-well plate (polystyrene Nunclon™ clear TC plate, flat bottom, Greiner, The Netherlands) at a concentration of $1 \times 10^5$ cells/well and incubated overnight in RPMI at 37° C. in a humidified atmosphere containing 5% $CO_2$ (unless specified otherwise). The cells were subsequently incubated overnight in 200 µl of RPMI containing gentamicin (15.6 to 1000 µg/ml), or incubated for 2 hours in RPMI containing photosensitizer $TPPS_{2a}$ (0.1 to 0.4 µg/ml) (PCI Biotech AS, Norway) which was replaced with refresh RPMI in order to remove unbound $TPPS_{2a}$ before incubation of another 2 hours. Raw 264.7 cells incubated in RPMI all the time were used as controls. The cells were protected from light using aluminium foil apart from illumination of 15 minutes using LumiSource (PCI Biotech AS, Norway). After illumination, cells were incubated in refresh RPMI for 24 hours. The effect of gentamicin and of $TPPS_{2a}$ on the metabolic activity of Raw 264.7 cells was tested using MTT at 24 hours after incubation or by WST-1 assay directly and at 24 hours after illumination, respectively, according to the manufacturer's instruction (Cell MTT or WST-1 assay kit, Sigma-Aldrich, The Netherlands). In order to test the effect of $TPPS_{2a}$ alone or combined with *S. epidermidis* on the viability of Raw 264.7 cells, cells were allowed to phagocytose bacteria for 45 minutes (phagocytosis assay is described in detail below) before incubation in 200 µl of RPMI containing 0.25 µg/ml $TPPS_{2a}$ for 2 hours, or incubated in 200 µl of RPMI only containing $TPPS_{2a}$ all the time (no bacteria). The cells were then washed with refresh RPMI and subsequently illuminated for 5, 10 or 15 minutes, or not illuminated. Cells only treated with illumination were used as controls. The influx of propidium iodide was measured to quantify the loss of cell viability directly or at 24 hours after illumination.

Phagocytosis of *S. epidermidis* by Raw 264.7 Cells

After culture *S. epidermidis* bacteria were pelleted, re-suspended in 1.5 ml of PBS mixed with 0.5 ml of human serum (H1 serum, Cat N14-402E, Bio Whittaker, The Netherlands) and incubated for 20 minutes for opsonization. The inoculum was adjusted to $1.8 \times 10^8$ CFU/ml with RPMI. Medium of cells was replaced by 40 µl of the bacterial inoculum (bacteria to cell ratio of 40:1) and phagocytosis was allowed to proceed for 45 minutes. Raw 264.7 cells were then gently washed four times with 60 µl, and with a final wash with 200 µl of preheated PBS (37° C.) to prevent carry-over of planktonic *S. epidermidis*, which was always found in less than 0.5% of the numbers of retrieved intracellular bacteria after these washing steps. Raw 264.7 cells were detached by incubation in 100 µl of RPMI containing 0.5 mM EDTA. Detached cells were transferred to a vial and lysed with 40 µl of 1% saponine by incubation in a waterbath sonicator for 5 minutes (Transsonic 460, Elma Schmldbaur GmbH, Germany). The sonicate was centrifuged, and the pelleted bacteria were washed repeatedly and re-suspended in PBS before quantitative culture of serial 10-fold dilutions. Intracellular surviving *S. epidermidis* in Raw 264.7 cells were expressed as numbers of CFU per well.

Intracellular Antimicrobial Activity Assay

After phagocytosis, Raw 264.7 cells were incubated in 200 µl of RPMI either containing gentamicin alone (1, 10 or 30 µg/ml) or combined with $TPPS_{2a}$ (0.25 µg/ml) for 2 hours, with non-treated cells incubated in RPMI or RPMI only containing $TPPS_{2a}$ as controls. For cells incubated with $TPPS_{2a}$, medium was replaced with refresh RPMI containing gentamicin with the identical concentrations before incubation of another 2 hours in order to remove unbound $TPPS_{2a}$. Cells were then incubated in refresh RPMI containing 1 µg/ml gentamicin, illuminated for 10 or 15 minutes with non-illuminated cells as controls. After illumination, cells were incubated overnight, lysed before quantitative culture of surviving bacteria.

Preparation of Fluorescently Labelled Gentamicin

An excess of gentamicin (in $K_2CO_3$, pH 9) (Sigma-Aldrich) was mixed with Alexa Fluor 405 succinimidyl ester (Life Technologies) to minimize the possibility of labelling individual gentamicin molecules with more than one Alexa Fluor 405 molecule. After conjugation, the reaction mixture was separated by reversed phase chromatography using a C-18 column to purify the conjugate from unconjugated gentamicin and Alexa Fluor 405 molecules. The isolated Alexa Fluor 405 labelled gentamicin was aliquoted, lyophilized, and stored in the dark at −20° C. until used.

Confocal Fluorescence Microscopy of Intracellular Distribution of Gentamicin and Photosensitizer in Raw 264.7 Cells After overnight culture, $3.0 \times 10^5$ cell/well Raw 264.7 cells were seeded at the bottom of a culture dish (MatTek Glass Bottom Culture Dish, U.S.) and incubated overnight in 1 ml of RPMI containing 10 µg/ml gentamicin alone or combined with 1 µg/ml $TPCS_{2a}$ (PCI Biotech AS, Norway). The cells were then gently washed with PBS repeatedly, illuminated for 2 minutes and covered with the Prolong® Gold antifade reagent (Life technologies, The Netherlands) for confocal microscopy (SP5, Leica, The Netherlands).

Zebrafish Husbandry and Maintenance

Adult wild type (WT) or transgenic (Tg) zebrafish were handled in compliance with the local animal welfare regulations approved by the local animal welfare committee (DEC). The maintenance of adult zebrafish and embryos was described earlier (Zhang et al., 2017, *J. Biomed. Mater. Res. A.*, 105(9), p2522-2532).

Injection into the Blood Circulation of Zebrafish Embryos

Injection into the blood circulation of zebrafish embryos via either the blood island or the duct of Cuvier (Benard et al., 2012, *Journal of visualized experiments: JoVE*, 61) was performed following the injection procedure described earlier (Zhang et al., 2017, supra). The volume of liquid per injection was adjusted to 1 nl for all injections in the present study.

Toxicity test of gentamicin alone or combined with $TPCS_{2a}$ in zebrafish embryos Gentamicin or $TPCS_{2a}$ solution (both in PBS) or mixtures were injected into WT zebrafish embryos at 32 hours post fertilization (hpf). PBS was injected into control embryos. The embryos were protected from light using aluminium foil apart from illumination for 10 minutes using LumiSource, at 34 hpf. Survival of embryos (heartbeat, movement) was monitored daily until 6 dpi.

Dose Finding of S. aureus for Zebrafish Embryo Infection

Wild type zebrafish embryos were injected with graded inocula of S. aureus ATCC 49230 at 30 hpf, and individually maintained in 200 µl of E3 medium. Medium was refreshed daily. The injected doses were checked by quantitative culture of 5-6 embryos per group, crushed using a MagNA lyser (Roche, The Netherlands). Survival was monitored daily until 4 dpi.

Visualization of Co-Localization of Phagocytes and Bacteria in Zebrafish Embryos Inoculum of S. aureus RN4220-GFP was intravenously injected into zebrafish embryos of the Tg line (lyzc:DsRed) featuring red fluorescently labelled neutrophils (Hall et al., 2007, BMC Dev. Biol., 7, p42), or of the Tg line (fms:Gal4: mCherry) featuring red fluorescently labelled macrophages (Gray et al., 2011, Thromb. Haemostasis, 105(5), p811-819) via the duct of Cuvier at 2 days post fertilization (dpf). At 2 hours post injection images were recorded under bright field, with FITC and mCherry filters using a fluorescence microscope (LM 80, Leica, The Netherlands).

Treatments of S. aureus-Infected Zebrafish Embryos with Gentamicin Alone or Combined with $TPCS_{2a}$ Wild type zebrafish embryos were intravenously injected with a suitable dose of S aureus ATCC 49230 via the blood island at 30 hpf, and randomly divided into groups for different treatments. At 32 hpf 1 nl of PBS solution containing gentamicin alone (0.05, 0.1 or 0.4 µg/ml) or combined with 0.25 µg/ml $TPCS_{2a}$ (to provide $2.5 \times 10^{-3}$ ng) was intravenously injected. Control embryos received PBS injections. The embryos were protected from light using aluminium foil apart from illumination of 10 minutes, at 34 hpf, and separately maintained in E3 medium, which was refreshed daily. Survival was monitored until 6 dpi.

Statistical Analysis

For in vitro toxicity testing as well as killing of intracellular bacteria in Raw 264.7 cells, differences between multiple groups and the same group for comparison were analyzed using Dunnett's multiple comparisons test. Differences between groups designated for pairwise comparison were analyzed using or Sidak's multiple comparisons test. Percent survival of embryos was evaluated using Kaplan-Meier method. Differences between pairs of survival curves were analyzed using log rank test. Differences were considered significant for P value<0.05. All analyses were performed using Graphpad Prism 7.0.

Results

Effect of Gentamicin and $TPPS_{2a}$ on the Metabolic Activity of Raw 264.7 Cells In order to perform intracellular killing assays, permissive concentrations of gentamicin and $TPPS_{2a}$ for Raw 264.7 cells were assessed by MTT and WST-1 assay, respectively. Extracellular concentrations of gentamicin up to 250 µg/ml did not reduce the metabolic activity of Raw 264.7 cells after incubation of 24 hours, which was therefore chosen as the maximum concentration of gentamicin in further experiments.

The possible inhibition of metabolic activity of Raw 264.7 cells by photosensitizer $TPPS_{2a}$ was assessed directly (T=0) or at 24 hours after illumination for 15 minutes (T=24). $TPPS_{2a}$ was tested at 0, 0.1, 0.2, 0.25, 0.3 and 0.4 µg/ml. Without illumination, the highest tested concentration of $TPPS_{2a}$, 0.4 µg/ml, did not reduce the metabolic activity at either time point. After illumination, concentrations of $TPPS_{2a}$ up to 0.25 µg/ml did not reduce the metabolic activity of Raw 264.7 cells at either time point (data not shown). Hence, 0.25 µg/ml was chosen as the maximum concentration of $TPPS_{2a}$ in further experiments.

In order to investigate the potentially negative effect of PCI treatment alone or combined with infection on cell viability, Raw 264.7 cells were treated with $TPPS_{2a}$ alone (0.25 µg/ml) or with $TPPS_{2a}$ in presence of S. epidermidis ($TPPS_{2a}$+S. epidermidis), (bacteria to cell ratio of 40:1) and illuminated for 5, 10 or 15 minutes. Non-treated but illuminated cells were used as controls. The influx of propidium iodide was measured to quantify loss of viability directly (T=0) and at 1 hour after illumination (T=1). Illumination as such did not influence cell viability. Treatment with $TPPS_{2a}$ caused a significant reduction of cell viability upon illumination for 5, 10 or 15 minutes (data not shown). Similar results were obtained for cells with $TPPS_{2a}$+S. epidermidis illuminated for 10 or 15 minutes (data not shown). Although reduction of viability of cells with $TPPS_{2a}$+S. epidermidis that illuminated for 5 minutes was also observed, it was not statistically different from the control group without illumination (data not shown).

Enhanced Killing of Intracellular S. epidermidis by Gentamicin in Raw 264.7 Cells by PCI To investigate whether $TPPS_{2a}$-PCI enhanced the killing of intracellular S. epidermidis by gentamicin, S. epidermidis-infected Raw 264.7 cells were exposed to $TPPS_{2a}$ only (0.25 µg/ml), to gentamicin only (1, 10 or 30 µg/ml) or to the respective gentamicin-$TPPS_{2a}$ combinations (FIG. 1). Gentamicin-$TPPS_{2a}$ combinations did not show an effect on the killing of intracellular bacteria upon illumination of 5 minutes (data not shown). Therefore, cells were illuminated for 10 or 15 minutes, with non-illuminated cells and non-treated, illuminated cells as controls. Without illumination, none of the treatments caused reduction of the numbers of intracellular bacteria in Raw 264.7 cells as compared to the non-treated group. With illumination, treatment with $TPPS_{2a}$ only did not affect intracellular survival of S. epidermidis as compared to the non-treated illuminated group, indicating that light-triggered activation of $TPPS_{2a}$ as such did not kill intracellular bacteria. Treatment with gentamicin only also did not kill intracellular S. epidermidis, regardless of the gentamicin concentration and the time of illumination. With illumination of 10 minutes, $TPPS_{2a}$-PCI significantly enhanced the killing by 30 µg/ml gentamicin (1 log reduction of the numbers of intracellular bacteria), but not by 10 µg/ml gentamicin. With illumination of 15 minutes, killing of intracellular S. epidermidis in Raw 264.7 cells treated with 10 and 30 µg/ml gentamicin combined with $TPPS_{2a}$ was significantly increased to 1 and 2.5 log reduction, respectively.

Intracellular Distribution of Gentamicin and TPCS$_{2a}$ in Raw 264.7 Cells With and Without Illumination To investigate whether PCI induced intra-cytosolic release of gentamicin upon illumination, intracellular distribution of gentamicin and the photosensitizer TPCS$_{2a}$ in Raw 264.7 cells with and without illumination was visualized (FIG. 2). TPCS$_{2a}$ absorbs red light and therefore is suitable for applications in vivo. Hence, TPCS$_{2a}$ was selected for this cell study and in vivo studies with zebrafish embryos. Without illumination, both gentamicin and TPCS$_{2a}$ localized within cellular compartments in the periphery of the cells, likely endocytic vesicles. After illumination both agents were released into the cytosol. Gentamicin seemed to accumulate at the nuclei of the Raw 264.7 cells.

Toxicity of Gentamicin and TPCS$_{2a}$ Alone or in Combination to Zebrafish Embryos To test their toxicity to zebrafish embryos, the effect of injection of graded doses of gentamicin (Doses ranging from 0.16 to 16 ng per 1 nl of PBS were injected per embryo, using 1 nl of PBS as control), TPCS$_{2a}$ (Doses of $2.5*10^{-2}$, $2.5*10^{-3}$ and $2.5*10^{-4}$ ng per 1 nl of PBS were injected per embryo, using 1 nl PBS as control) and gentamicin-TPCS$_{2a}$ combinations (Doses of 1.6 and 0.8 ng GEN alone or combined with $2.5*10^{-3}$ ng TPCS$_{2a}$ (in 1 nl of PBS) were injected, using 1 nl of PBS injection as control) on survival was assessed. Gentamicin and TPCS$_{2a}$ both showed a dose-dependent toxicity, with maximal non-toxic concentrations of 2 and $2.5*10^{-3}$ ng/embryo, respectively (data not shown). Combinations of 1.6 or 0.8 ng/embryo gentamicin and $2.5*10^{-3}$ ng/embryo TPCS$_{2a}$ did not reduce survival of embryos (data not shown). Initial group sizes ranged from 33 to 36 embryos.

Dose Finding of *S. aureus* for Zebrafish Embryo Infection and Visualization of Cell-Pathogen Interaction In Vivo To assess suitable doses of *S. aureus* for the infection experiments with zebrafish embryos, graded inocula were injected into the blood circulation at 30 hours post-fertilization. The median CFU numbers of injected *S. aureus* were 150, 500, 2750 and 7500 CFU/embryo for the groups with intended challenge doses of 100, 500, 3000 and 6000 CFU/embryo, respectively. The variation of CFU numbers retrieved within groups was minor (FIG. 3A). Death of *S. aureus*-infected embryos was proportional to the inoculum dose (FIG. 3B). The dose of 3000 CFU/embryo caused approximately 50% death of the embryos at 4 days post injection (FIG. 3B), which is suitable to assess the efficacy of antibiotic treatments, and therefore was chosen for further experiments.

Survival of *S. aureus*-Infected Embryos Treated with Gentamicin Alone or Combined with TPCS$_{2a}$ To investigate whether PCI enhanced the antimicrobial efficacy of gentamicin against Staphylococcal infection in vivo, *S. aureus*-infected zebrafish embryos were treated with gentamicin alone or combined with TPCS$_{2a}$. The median CFU number of injected *S. aureus* was determined to be 2850 CFU/embryo (data not shown). All treatments with gentamicin (without or with TPCS$_{2a}$) significantly improved the survival as compared to the PBS mock treatment (FIG. 4). Addition of TPCS$_{2a}$ to 0.1 ng gentamicin significantly improved the treatment outcome compared to treatment with 0.1 ng gentamicin alone, resulting in levels of survival similar to those obtained with 0.4 ng gentamicin treatment. This shows that PCI enhances the antimicrobial activity of gentamicin against *S. aureus* infection and lowers the required dose for efficacy. However, a minimal gentamicin dosing is necessary to observe the enhancing effect of TPCS$_{2a}$, since TPCS$_{2a}$ did not improve the efficacy when embryos were treated with 0.05 ng gentamicin (FIG. 4).

Conclusion

PCI has been shown to enhance intracellular activity of gentamicin, an antibiotic with limited antimicrobial efficacy inside cells, against Staphylococci both in vitro and in vivo. In Raw 264.7 cells, PCI induced cytosolic release of gentamicin after illumination and increased eradication of phagocytosed *S. epidermidis*. In a zebrafish embryo model with *S. aureus* internalized by phagocytes, PCI enhanced the efficacy of gentamicin treatment against (intracellular) *S. aureus* infection and lowered the required dose. These results are the first to demonstrate that PCI enhances the intracellular activity of antibiotics against infection involving intracellular bacteria.

In the present study, although some cytotoxicity to Raw 264.7 cells was observed upon illumination, treatment with PCI-gentamicin combinations of zebrafish embryos did not negatively influence their survival following treatment. These results indicate that PCI may cause moderate levels of damage to the cells in vitro, but at levels required for its antibiotic-enhancing activity in vivo does not cause death of zebrafish embryos.

This allows site-specific application of PCI mediated treatment of (intracellular) infection upon illumination applied to the infected areas. As a result the potential side-effects of the photosensitizers against normal tissues and cells in the non-illuminated areas can be strongly reduced.

In the reported experiments, in the in vitro assay with Raw 264.7 cells it was necessary for the cells to remain alive after phagocytosis of bacteria, in order to be able to register intracellular killing after treatment. Therefore, *S. epidermidis* was used, since these bacteria can survive but do not vigorously proliferate inside macrophages in vitro (Lemaire et al., 2010, *Antimicrob. Agents Ch.*, 54(6), p2549-2559). In the zebrafish embryo model however, the embryos should be rescued from rapid death by the antimicrobial treatment, and thus a bacterial pathogen capable of killing the embryos was needed. *S. epidermidis* did not kill the embryos even after intravenous injection of a very high inoculum of approximately $3.8\times10^4$ CFU per embryo (data not shown). Therefore, *S. aureus* known for its ability to cause rapidly disseminating infection in zebrafish embryos (Prajsnar et al., 2008, supra) was used for the present in vivo studies. In the early developmental stages of zebrafish embryos, clearance of *S. aureus* is mainly dependent on phagocytosis by macrophages and neutrophils (Prajsnar et al., 2008, supra) which are both functional in embryos at 30 hours post fertilization (Trede et al., 2004, *Immunity*, 20(4), p367-379). Similar to other studies using zebrafish embryos (Prajsnar et al., 2008, supra; Prajsnar et al., 2012, supra), co-localization of *S. aureus* and phagocytic cells was observed as soon as at 2 hours post injection in the present study, implying that efficient phagocytosis had occurred during this period. This underlines the relevance of the zebrafish embryo infection model for testing the intracellular activity of antibiotics.

The quantity of antibiotics accumulating inside cells is essential for the efficiency of killing of intracellular bacteria (Seral et al., 2003, supra; and Barcia-Macay et al., 2006, *Antimicrob. Agents Ch.,* 50(3), p841-851). Hence, in the in vitro model of Raw 264.7 cells engulfing *S. epidermidis,* the cells were exposed to relatively high concentrations of gentamicin (10 and 30 µg/ml) for 2 hours. Even with such high extracellular concentrations, gentamicin did not kill the intracellular *S. epidermidis* bacteria. Strikingly, combining the treatment with the use of PCI significantly improved the antimicrobial efficacy of gentamicin (FIG. 1). A similar efficacy-enhancing effect of PCI was observed in vivo in the zebrafish embryo *S. aureus* infection model. PCI significantly enhanced the outcome of gentamicin treatment of *S. aureus*-infected embryos and lowered the required dose (FIG. 4). However, no effect of PCI on the efficacy of the lowest dose of gentamicin was observed either in vitro or in vivo, indicating that a sufficient amount of intracellular gentamicin is a prerequisite. Increasing the uptake period of gentamicin is expected to achieve PCI-enhanced efficacy at low antibiotic doses.

Interestingly, the liberated gentamicin molecules seemed to accumulate at the nuclei of Raw 264.7 cells after illumination (FIG. 2). This observation is in line with the reported result that gentamicin can bind to the nuclei of kidney cells (Myrdal et al., 2005, *Hearing Res.,* 204(1-2), p156-169). Although theoretically such binding may reduce the amount of free gentamicin in the cytosol, enhanced efficacy of gentamicin by PCI was still observed. Therefore, the enhancement of intracellular activity of antibiotics, which do not show nuclear binding, by PCI, might be even more significant.

Different subcellular locations of bacteria and antibiotic molecules also potentially influence the intracellular activity of antibiotics (Carryn, 2003, supra). After phagocytosis, several bacterial species including *staphylococci* are mainly entrapped in phagosomes and cannot be efficiently eradicated by antibiotics taken up in other vesicles (Seral et al., 2003, supra; Barcia-Macay et al., 2006, supra; and Bernardo and Simons, 2009, *Cytom. Part A,* 77A(3), p10). In the present study, it is speculated that after rupturing the endosomes containing antibiotics, (part of) the dissociated photosensitizers may re-localize to the membranes of phagosomes containing bacteria and also rupture these membranes during the illumination period. Therefore, at least a portion of the bacteria residing in phagosomes may be released into the cytosol and killed by gentamicin more rapidly. It is also possible that during PCI the vesicles ruptured by the light-activation of photosensitizer might intracellularly fuse with intact other vesicles to cause the intact ones also to become leaky/ruptured, even without additional illumination. Such fusion therefore may also (partially) contribute to the cytosolic release of both bacteria and antibiotics, facilitating the intracellular antimicrobial action. Thus, based on these experiments, PCI can be expected also to improve the intracellular activity of other antibiotics such as vancomycin, oritavancin and various macrolides. This consequently may prevent resistance development due to low, permissive concentrations of such antibiotics inside cells. PCI therefore can increase the number of antibiotics which can successfully treat intracellular infection. In addition, the required doses of antibiotics may be reduced using PCI.

The present experiment illustrates that PCI may be used to improve the antibiotic treatment of intracellular infection and help prevent resistance development.

EXAMPLE 2

Enhanced Antibacterial Efficacy of Vancomycin against Intracellular Staphylococcal Infection by PCI Similar experiments were conducted, compared to those in Example 1, except that vancomycin was used as the antibacterial agent.

Methods and Results

PCI Re-Localises Vancomycin from Andocytic Vesicles to the Cytosol in Macrophages To investigate if PCI treatment could release vancomycin from endocytic vesicles in macrophages, an experiment was set up with the RAW 264.7 macrophage cell line studying the intracellular localization of fluorescently labeled vancomycin and $TPCS_{2a}$ before and after illumination.

The macrophage cell line RAW 264.7 was incubated with 1 µg/ml $TPCS_{2a}$ and 50 µg/mL BODIPY® FL-Vancomycin (Life Technologies) (Vanco-FL) for 18 h. The cells were washed 2 times in drug-free medium and incubated for 4 h in drug-free medium before illumination with LumiSource for 120 s. The intracellular localization of $TPCS_{2a}$ and BODIPY® FL-Vancomycin was analysed by fluorescence microscopy before (A) and after (B) illumination using the following filter settings:

$TPCS_{2a}$: Excitation: Band-pass: 395-440 nm, dichroic beam splitter 460 nm.

Emission: Long-pass 620 nm. BODIPY: Excitation: Band-pass: 450-490 nm.

Emission: Band-pass 500-550 nm. The results are shown in FIG. 5.

It can be seen that before illumination (FIG. 5A) both vancomycin and $TPCS_{2a}$ were localized in small spots inside the cells, corresponding to endocytic vesicles, and vancomycin and $TPCS_{2a}$ were to a large degree co-localised in the same vesicles (bright spots in the "Merge" panel). After illumination, vancomycin and $TPCS_{2a}$ were released from the endocytic vesicles, something that can be clearly seen from FIG. 5B by the disappearance of the discrete intracellular spot and the diffuse localization of the fluorescent compounds in the whole cell body. This shows that PCI can release vancomycin from intracellular vesicles into the cytosol of the cell.

The effect of PCI is seen even more clearly in FIG. 6, where the vancomycin-BODIPY fluorescence can also be quantitatively compared before and after PCI. It can be seen that in addition to inducing an intracellular re-localisation of vancomycin from endocytic vesicles to the cell cytosol, PCI also seems to induce a strong increase in the fluorescence signal from the vancomycin-BODIPY. The probable reason for this is that the vancomycin molecules are aggregated inside the endosomes and they disaggregate upon release into the much larger distribution volume in the cytosol. It is well known that aggregation of fluorescent molecules leads to quenching of the fluorescence, and that the fluorescence from fluorophores in aggregates will increase substantially upon disaggregation. Since aggregated molecules in general will be unable to interact with therapeutic targets the disaggregation seen after PCI will add further to the enhancement of antimicrobial activity that can be achieved with PCI.

PCI Enhances the Anti-Microbial Effect of Vancomycin in Zebrafish Embryos

The toxicity of vancomycin (Vanco) alone or combined with $TPCS_{2a}$ and illumination (T) for non-infected zebrafish embryos was examined. Doses of vancomycin (0.4, 1.6 or 6.4 ng per 1 nl of PBS), or combined with $2.5*10^{-3}$ ng $TPCS_{2a}$ per 1 nl of PBS, were injected per embryo. After injections, zebrafish embryos were maintained group-wise in petri-dishes containing E3 medium. The petri-dishes to be illuminated were placed on the Lumisource illumination device and embryos were illuminated for 10 minutes. The initial group sizes were 27 to 29 embryos.

Injection of vancomycin with doses of 0.4 to 6.4 ng per non-infected embryo show a dose-dependent toxicity to zebrafish embryos, causing approximately 5% to 20% of the embryo death at 6 days post injection (dpi), data not shown. The combinations of vancomycin and $TPCS_{2a}$/illumination caused stronger toxicity, as approximately 20-40% of the embryos were dead at 6 dpi (data not shown).

To investigate whether PCI enhanced the antimicrobial efficacy of vancomycin against *Staphylococcus aureus* infection, *S. aureus*-infected zebrafish embryos were treated with vancomycin alone (0.4 ng) or combined with $TPCS_{2a}$ ($2.5*10^{-3}$ ng). PBS mock treatment was used as control. After injections, zebrafish embryos were maintained group-wise in petri-dishes containing E3 medium. The petri-dishes were placed on the Lumisource illumination device and embryos were illuminated for 10 minutes. Initial group sizes were 29 or 30 embryos. The difference between survival of the vancomycin alone group and the vancomycin-$TPCS_{2a}$/illumination group was analyzed using Log-rank test, $*p\leq0.033$.

The median CFU number of injected *S. aureus* was determined to be 4300 CFU/embryo. It can be seen (FIG. 7) that while vancomycin alone had no effect on the survival of the infected embryos, the infection-mediated reduction in survival was significantly delayed by the vancomycin+$TPCS_{2a}$/illumination (T) combination. Of note, according to the toxicity test (discussed above, data not shown), the vancomycin+$TPCS_{2a}$/illumination combination per se caused more embryos death than vancomycin alone (at least 15% higher), meaning that the enhancement effect of PCI on the antimicrobial effect of vancomycin probably is even greater than what is apparent from FIG. 7.

The invention claimed is:

1. A method of treating an intracellular bacterial infection, comprising contacting the cell(s) which are infected with an antibacterial agent and a photosensitizing agent and irradiating the cell(s) with light of a wavelength effective to activate the photosensitizing agent which releases the antibacterial agent into the cytosol of the cell(s) and the released antibacterial agent kills, damages or prevents the replication of bacteria in said cell(s).

2. The method as claimed in claim 1 wherein said method is performed in vivo and said cell(s) is in a subject.

3. The method as claimed in claim 1 wherein said contacting step is performed for 15 minutes to 4 hours.

4. The method as claimed in claim 1 wherein said photosensitizing agent is an amphiphilic porphyrin, chlorin, bacteriochlorin or phthalocyanine.

5. The method as claimed in claim 4 wherein said photosensitizing agent is selected from tetraphenyl chlorin disulfonate ($TPCS_{2a}$), aluminium phthalocyanine disulfonate ($AlPcS_{2a}$), tetraphenylporphine disulfonate ($TPPS_{2a}$) and tetraphenyl bacteriochlorin disulfonate ($TPBS_{2a}$).

6. The method as claimed in claim 1 comprising locally delivering the dose of photosensitizing agent in an amount ranging from 0.0025 to 250 µg.

7. The method as claimed in claim 1 wherein the cell(s) is irradiated for between 5 and 60 minutes.

8. The method as claimed in claim 1 comprising locally delivering the dose of the antibacterial agent in an amount ranging from 25 to 10000 µg.

9. The method as claimed in claim 1 wherein the antibacterial agent is an aminoglycoside, a glycopeptide or a macrolide.

10. The method as claimed in claim 1 wherein the bacterial infection is caused by a *Staphylococcus, Mycobacterium, Pseudomonas* or *Escherichia* bacteria.

11. The method as claimed in claim 1 wherein the bacterial infection is a biomaterial-associated infection.

12. The method as claimed in claim 1 wherein the bacterial infection is osteomyelitis, bacteremia, tuberculosis, Q-fever, endocarditis, a (sub)cutaneous skin or mucosal infection/damage, an oral and nasal infection or peri-implantitis.

13. The method as claimed in claim 1 wherein the cell(s) is present on, or adjacent to, a biomaterial.

14. The method as claimed in claim 13, wherein the antibacterial agent and/or the photosensitizing agent is provided on or within the biomaterial.

15. The method as claimed in claim 2 wherein said subject is a mammal.

16. The method as claimed in claim 2 wherein said subject is a cow and the bacterial infection is *S. aureus* mastitis.

17. The method as claimed in claim 1 wherein said cell(s) is contacted with said antibacterial agent and photosensitizing agent simultaneously, separately or sequentially.

18. The method as claimed in claim 9 wherein the antibacterial agent is gentamicin or vancomycin.

19. The method as claimed in claim 1 comprising locally delivering the dose of photosensitizing agent in an amount ranging from 1 to 250 µg.

20. The method as claimed in claim 2 wherein said subject is a human.

21. The method as claimed in claim 17 wherein when said method is performed in vivo said contact is achieved by topical, intradermal, subcutaneous or intravenous administration of said antibacterial agent and said photosensitizing agent.

22. The method as claimed in claim 11 wherein the biomaterial is selected from the group consisting of a medical device, instrument, implement or equipment, a prosthetic or material, tissue and wound dressing.

23. The method as claimed in claim 13 wherein the biomaterial is selected from the group consisting of a medical device, instrument, implement or equipment, a prosthetic or material, tissue and wound dressing.

* * * * *